(12) United States Patent
Kuwabara

(10) Patent No.: US 8,848,876 B2
(45) Date of Patent: Sep. 30, 2014

(54) RADIOGRAPHIC APPARATUS

(75) Inventor: Shoji Kuwabara, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 348 days.

(21) Appl. No.: 13/144,374

(22) PCT Filed: Feb. 10, 2009

(86) PCT No.: PCT/JP2009/000535
§ 371 (c)(1),
(2), (4) Date: Jul. 13, 2011

(87) PCT Pub. No.: WO2010/092615
PCT Pub. Date: Aug. 19, 2010

(65) Prior Publication Data
US 2011/0274252 A1  Nov. 10, 2011

(51) Int. Cl.
*G21K 1/00* (2006.01)
*A61B 6/00* (2006.01)
*G21K 1/02* (2006.01)
*H04N 5/32* (2006.01)

(52) U.S. Cl.
CPC ............. *G21K 1/025* (2013.01); *A61B 6/4291* (2013.01); *A61B 6/588* (2013.01); *H04N 5/32* (2013.01); *A61B 6/583* (2013.01)
USPC .......................................... 378/155; 378/154

(58) Field of Classification Search
CPC ..................................................... A61B 6/4291
USPC .......................................................... 378/155
See application file for complete search history.

(56) References Cited

U.S. PATENT DOCUMENTS

2004/0202279 A1* 10/2004 Besson et al. .................. 378/37
2008/0080673 A1*  4/2008 Yamakita ...................... 378/155

FOREIGN PATENT DOCUMENTS

JP          2002-257939 A      9/2002

* cited by examiner

*Primary Examiner* — Allen C. Ho
*Assistant Examiner* — Dani Fox
(74) *Attorney, Agent, or Firm* — Cheng Law Group, PLLC

(57) ABSTRACT

According to a radiographic apparatus of this invention, parameters obtained on an assumption that an X-ray tube 2 is moved Wd×m, which is an integral multiple of pixel pitch Wd, in a $B^-$ direction opposite to $B^+$ direction which is a direction of movement by Y-direction adjust screws of a moving mechanism, are corrected as parameters obtained when X-rays are emitted from the X-ray tube 2 in a state of a grid 6 having been moved Wd×m by the Y-direction adjust screws. This allows only the grid 6 to be moved without moving the X-ray tube 2. Therefore, parameters equivalent to the parameters which should be obtained when the X-ray tube 2 is moved are obtained by moving the grid 6, and position shifting can be reduced.

6 Claims, 14 Drawing Sheets

RADIOGRAPHIC APPARATUS

TECHNICAL FIELD

This invention relates to a radiographic apparatus for use as an X-ray fluoroscopic apparatus or X-ray CT apparatus, and more particularly to a technique for removing scattered radiation.

BACKGROUND ART

Conventionally, in order to prevent scattered X-rays (hereinafter called simply "scattered rays") transmitted through a subject or patient from entering an X-ray detector, a medical X-ray fluoroscopic apparatus or X-ray CT (computed tomography) uses a grid (scattered radiation removing device) for removing the scattered rays. However, even if the grid is used, a false image is produced by the scattered rays passing through the grid, and a false image by absorbing foil strips constituting the grid. Particularly where a flat panel (two-dimensional) X-ray detector (FPD: Flat Panel Detector) with detecting elements arranged in rows and columns (two-dimensional matrix form) is used as the X-ray detector, a false image such as a moire pattern is produced due to a difference between the spacing of the absorbing foil strips of the grid and the pixel spacing of the FPD, besides the false image by the scattered rays. In order to reduce such false images, a false image correction is needed. In order not to produce such a moire pattern, a synchronous grid has been proposed recently, which grid has absorbing foil strips arranged parallel to either the rows or the columns of the detecting elements, and in a number corresponding to an integral multiple of the pixel spacing of the FPD, and a correction method for use of this grid is also needed (see Patent Document 1, for example).

By way of correcting moire patterns, a method of image processing which includes smoothing, for example, is carried out nowadays. When false image correction is done to excess, the resolution of direct X-rays (hereinafter called simply "direct rays") also tends to lower. Therefore, an attempt to reduce false images reliably through image processing will lower the resolution of direct rays, resulting in less clear patient images. Conversely, when greater importance is placed on the resolution of direct rays to obtain clear patient images, the false images will not be reduced through image processing, which constitutes what is called a trade-off between image processing and clearness. Thus, a perfect false image processing is difficult. Regarding the correction of the scattered rays remaining despite use of a grid, various methods have been proposed but these have disadvantages such as involving a time-consuming correcting arithmetic operation.

Applicant herein has also proposed a radiographic apparatus having a function to process false images and acquire an image only of direct rays. This proposed radiographic apparatus (X-ray imaging apparatus in an embodiment) obtains, as false image processing parameters, before X-ray imaging, direct ray transmittances which are transmittances of direct rays before and after transmission through a grid, and rates of change relating to transmission scattered ray intensities which are scattered ray intensities after transmission through the grid. Based on a false image processing algorithm using the above parameters, an image only of direct rays can be acquired without false images resulting from the grid.

Patent Document 1

Unexamined Patent Publication No. 2002-257939

DISCLOSURE OF THE INVENTION

Problem to be Solved by the Invention

However, when application is made to actual medical apparatus such as apparatus used for diagnosis of the cardiac blood vessels (CVS: cardiovascular systems), for example, diagnosis (that is, X-ray imaging) is usually carried out using a C-arm. The C-arm is curved literally in the shape of character "C". The C-arm is constructed to support a radiation emitting device such as an X-ray tube at one end thereof, and to support an FPD at the other end. When the C-arm is rotated along a curving direction of the C-arm, the X-ray tube and the FPD revolve with the rotation. At the same time, X-ray images are picked up with the X-ray tube emitting X-rays and the FPD detecting the X-rays. At the time of X-ray imaging of a subject, despite the condition that a positional relationship between a X-ray focus of the X-ray tube, the grid and the FPD should be constant under normal circumstances, the rotation of the C-arm and the like cause a shift in the positional relationship between the X-ray focus, the grid and the FPD. This shift causes changes of parameter values from the values acquired in advance. When a false image processing is carried out by simply using the changed parameter values, a large false image will be formed. Therefore, for example, application to certain apparatus using a C-arm is difficult.

This invention has been made having regard to the state of the art noted above, and its object is to provide a radiographic apparatus which can reduce position shifting.

Means for Solving the Problem

To fulfill the above object, this invention provides the following construction.

A radiographic apparatus of this invention is a radiographic apparatus for obtaining a radiological image, having a radiation emitting device for emitting radiation; a scattered radiation removing device for removing scattered radiation; and a radiation detecting device having a plurality of detecting elements arranged in rows and columns for detecting the radiation; wherein the scattered radiation removing device is constructed to have a direction of arrangement of absorbing layers, which absorb the scattered radiation, parallel to at least one of a direction of the rows and a direction of the columns of the detecting elements, and to have each of the absorbing layers arranged parallel to a detecting plane of the radiation detecting device; the apparatus comprising a moving device for moving the scattered radiation removing device parallel to the direction of arrangement of the absorbing layers; a physical quantity calculating device for calculating physical quantities relating to radiation intensity based on detection by the radiation detecting device of the radiation after transmission through the scattered radiation removing device; and a correcting device for correcting physical quantities obtained on an assumption that the radiation emitting device is moved a predetermined distance in a direction opposite to a direction of movement by the moving device, as the physical quantities calculated by the physical quantity calculating device when radiation is emitted from the radiation emitting device in a state of the scattered radiation removing device having been moved the predetermined distance by the moving device.

When the radiation emitting device or the radiation detecting device is moved as in the prior art, position shifting will occur as noted hereinbefore. Particularly, the radiation emitting device is heavy, and when such heavy radiation emitting device is moved parallel to the direction of arrangement of the absorbing layers (of the scattered radiation removing device), even if moving distances are set finely, actual moving distances become different from the set moving distances. Then, a change has been made in the concept of carrying out radiation imaging by moving the radiation emitting device or the radiation detecting device, or using data obtained by moving the radiation emitting device or the radiation detecting device in the radiation imaging. Consequently, it has been contrived to move the scattered radiation removing device which is lighter than the radiation emission device and the radiation detecting device.

According to the radiographic apparatus of this invention, the scattered radiation removing device is constructed to have the direction of arrangement of the absorbing layers, which absorb scattered radiation, parallel to at least one of the direction of rows and the direction of columns of the detecting elements, and to have each absorbing layer arranged parallel to the detecting plane of the radiation detecting device. The moving device moves the scattered radiation removing device parallel to the direction of arrangement of the absorbing layers. Therefore, when the moving device moves the scattered radiation removing device a predetermined distance and radiation is emitted from the radiation emitting device, the physical quantities calculated by the physical quantity calculating device are obtained when radiation is emitted from the radiation emitting device in the state of the scattered radiation removing device having been moved the above predetermined distance by the moving device. On the other hand, assuming that the radiation emitting device is moved the predetermined distance in the opposite direction to the direction of movement by the moving device, the physical quantities which should be obtained on this assumption can be considered the same as the physical quantities calculated by the physical quantity calculating device when radiation is emitted from the radiation emitting device in the state of the scattered radiation removing device having been moved the above predetermined distance by the moving device. Therefore, the correcting device corrects the physical quantities which should be obtained on the assumption, as the physical quantities calculated by the physical quantity calculating device when radiation is emitted from the radiation emitting device in the state of the scattered radiation removing device having been moved the above predetermined distance by the moving device, which allows only the scattered radiation removing device to be moved, instead of moving the radiation emitting device. Therefore, physical quantities equivalent to the physical quantities which should be obtained when the radiation emitting device is moved are obtained by moving the scattered radiation removing device, and position shifting can be reduced.

In the above radiographic apparatus of the invention, the correction can be made as follows when the moving device is constructed capable of moving the scattered radiation removing device parallel to the direction of arrangement of the absorbing layers by an integral multiple of intervals between pixels forming the radiological image. That is, the correcting device is arranged to correct physical quantities obtained on an assumption that the radiation emitting device is moved an amount corresponding to the integral number of pixels in the direction opposite to the direction of movement by the moving device, as the physical quantities calculated by the physical quantity calculating device when radiation is emitted from the radiation emitting device in a state of the scattered radiation removing device having been moved the amount corresponding to the integral number of pixels by the moving device. When the predetermined distance of movement by the moving device is set to the integral multiple of the intervals between the pixels as described above, the interval between the position to which the radiation emitting device is virtually moved and the position to which the scattered radiation removing device is actually moved is related to the integral number of pixels. Thus, the physical quantities can be corrected accurately with no position shifting between the pixels.

In the above radiographic apparatus of the invention, one example of the physical quantities is direct ray transmittances which are transmittances before transmission and after transmission of direct radiation through the scattered radiation removing device obtained by actual measurement in the absence of a subject. In the case of this example, the physical quantity calculating device calculates the direct ray transmittances. Then, the correcting device is arranged to correct direct ray transmittances obtained on an assumption that the radiation emitting device is moved the predetermined distance in the direction opposite to the direction of movement by the moving device, as the direct ray transmittances calculated by the physical quantity calculating device when radiation is emitted from the radiation emitting device in a state of the scattered radiation removing device having been moved the predetermined distance by the moving device. By using the direct ray transmittances corrected as described above in the radiographic imaging, false image processing is carried out with the direct ray transmittances having no position shifting, thereby to remove false images due to position shifting.

In the above radiographic apparatus of the invention, another example of the physical quantities is rates of change relating to transmission scattered ray intensity which is scattered radiation intensity after transmission through the scattered radiation removing device. In the case of this example, the physical quantity calculating device calculates the rates of change. Then, the correcting device is arranged to correct rates of change obtained on an assumption that the radiation emitting device is moved the predetermined distance in the direction opposite to the direction of movement by the moving device, as the rates of change calculated by the physical quantity calculating device when radiation is emitted from the radiation emitting device in a state of the scattered radiation removing device having been moved the predetermined distance by the moving device. By using the rates of change corrected as described above in the radiographic imaging, false image processing is carried out with the rates of change having no position shifting, thereby to remove false images due to position shifting.

In the above radiographic apparatus of the invention, a further example of the physical quantities is the direct ray transmittances and rates of change noted above. In the case of this example, the physical quantity calculating device calculates the direct ray transmittances and the rates of change. Then, the correcting device is arranged to correct direct ray transmittances and rates of change obtained on an assumption that the radiation emitting device is moved the predetermined distance in the direction opposite to the direction of movement by the moving device, as the direct ray transmittances and the rates of change calculated by the physical quantity calculating device when radiation is emitted from the radiation emitting device in a state of the scattered radiation removing device having been moved the predetermined distance by the moving device. By using the direct ray transmittances and the rates of change corrected as described above in the radiographic imaging, false image processing is carried out with the direct ray transmittances and the rates of change having no position shifting, thereby to remove false images due to position shifting.

In the above radiographic apparatus of the invention, a further example of the physical quantities is pixel values allotted to respective pixels forming the radiological image and corresponding to radiation intensities detected by the radiation detecting device. In the case of this example, the physical quantity calculating device calculates the pixel values. Then, the correcting device is arranged to correct pixel values obtained on an assumption that the radiation emitting device is moved over the number of pixels corresponding to the predetermined distance in the direction opposite to the direction of movement by the moving device, as the pixel values calculated by the physical quantity calculating device when radiation is emitted from the radiation emitting device in a state of the scattered radiation removing device having been moved the number of pixels corresponding to the predetermined distance by the moving device.

Effects of the Invention

According to the radiographic apparatus of this invention, the scattered radiation removing device is constructed to have the direction of arrangement of the absorbing layers, which absorb scattered radiation, parallel to at least one of the direction of rows and the direction of columns of the detecting elements, and to have each absorbing layer arranged parallel to the detecting plane of the radiation detecting device. The moving device moves the scattered radiation removing device parallel to the direction of arrangement of the absorbing layers. The correcting device corrects the physical quantities obtained on an assumption that the radiation emitting device is moved a predetermined distance in the opposite direction to the direction of movement by the moving device, as the physical quantities calculated by the physical quantity calculating device when radiation is emitted from the radiation emitting device in the state of the scattered radiation removing device having been moved the above predetermined distance by the moving device, which allows only the scattered radiation removing device to be moved, instead of moving the radiation emitting device. Therefore, physical quantities equivalent to the physical quantities which should be obtained when the radiation emitting device is moved are obtained by moving the scattered radiation removing device, and position shifting can be reduced.

DESCRIPTION OF REFERENCES

Figure 1:
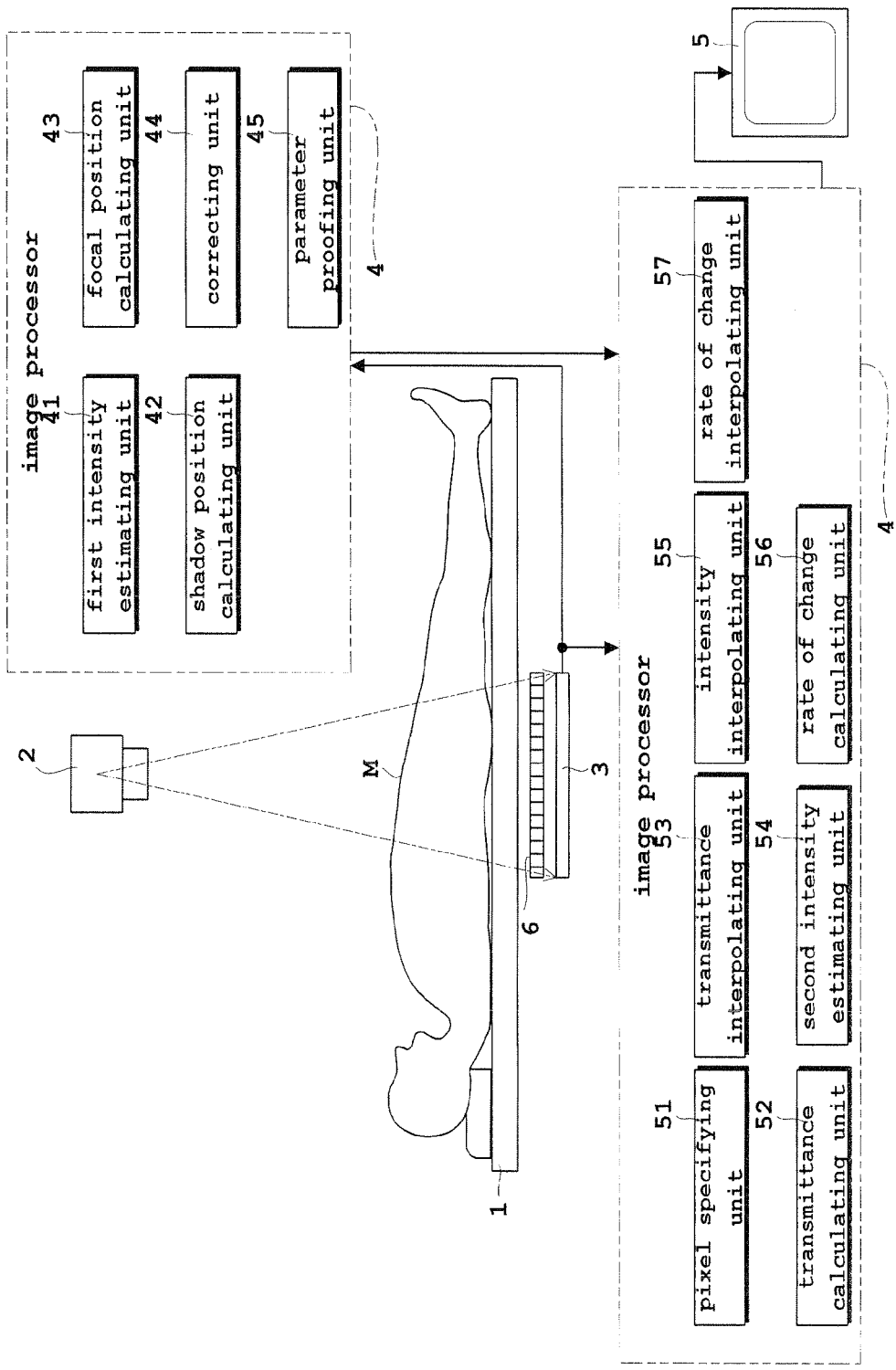
FIG. 1 is a block diagram of an X-ray imaging apparatus according to an embodiment.

2 . . . X-ray tube
3 . . . flat panel X-ray detector (FPD)
d . . . detecting elements
6 . . . grid
6a . . . absorbing foil strips
44 . . . correcting unit
52 . . . transmittance calculating unit
53 . . . transmittance interpolating unit
56 . . . rate of change calculating unit
57 . . . rate of change interpolating unit
60 . . . moving mechanism
60y . . . Y-direction adjust screws
Wd . . . pixel pitch
Cp . . . direct ray transmittances
Rcs . . . rates of change
M . . . subject

EMBODIMENT

Figure 2:
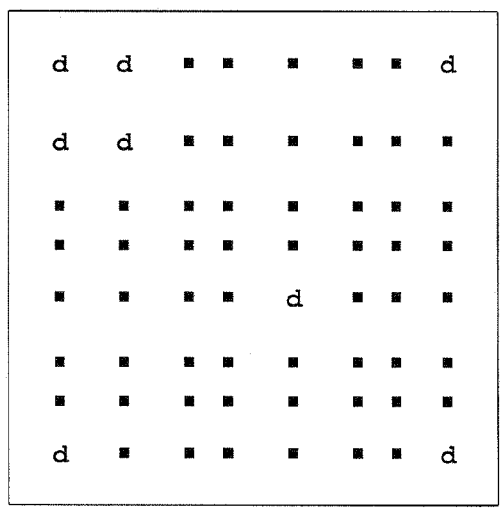
FIG. 2 is a schematic view of a detecting plane of a flat panel X-ray detector (FPD)
Figure 3:
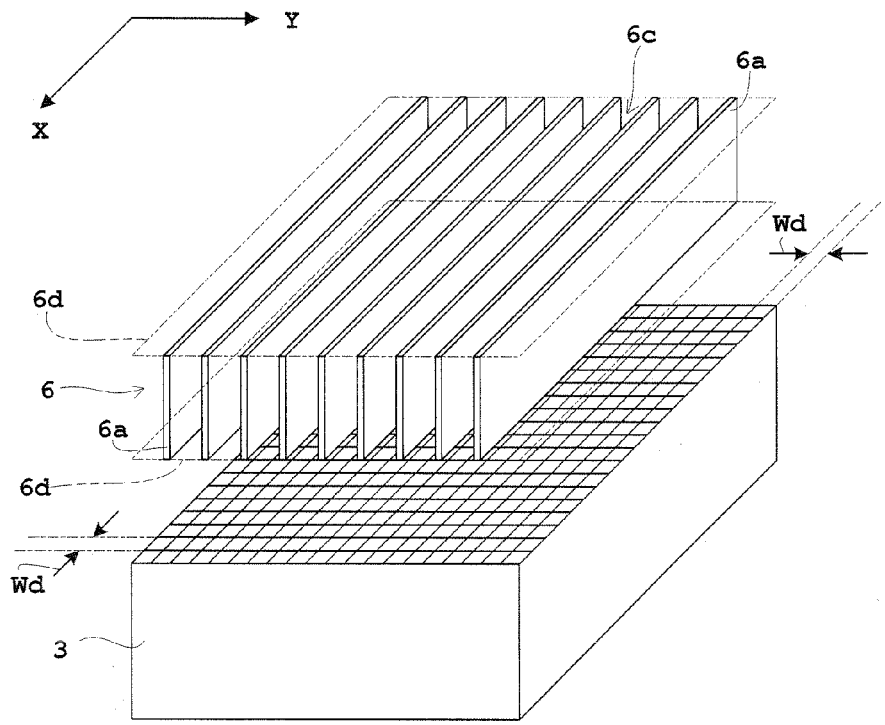
FIG. 3 is a schematic view of a common grid.
Figure 4:
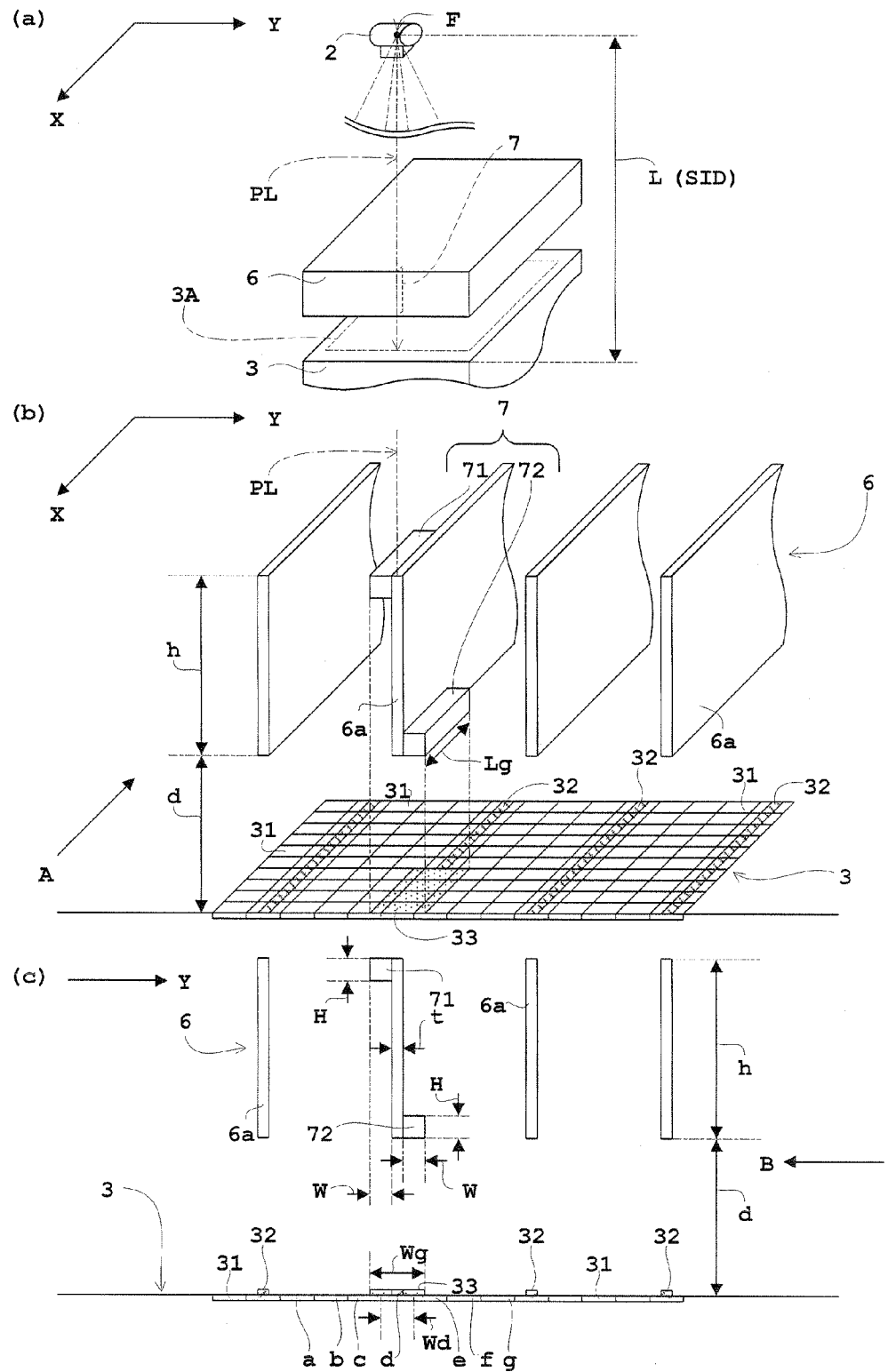
FIG. 4 (a) is a perspective view showing an overall outline of the grid, FPD and marking absorbers along with an X-ray tube, (b) is an enlarged view of the marking absorbers and adjacent components, and (c) is a sectional view seen from arrow A of (b)
Figure 5:
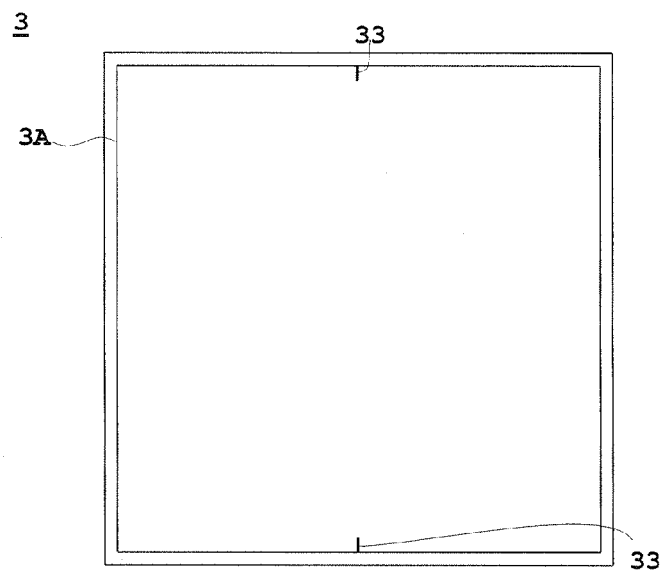
FIG. 5 is a schematic plan view illustrating an effective field of view area of the FPD.
Figure 6:
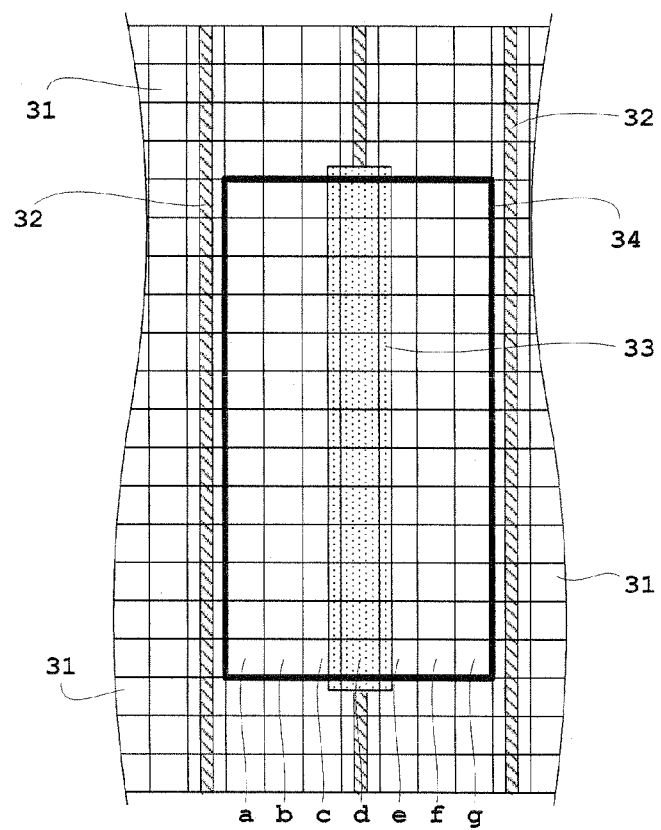
FIG. 6 is a schematic view showing a plurality of pixels centering on shadowed pixels.
Figure 7:
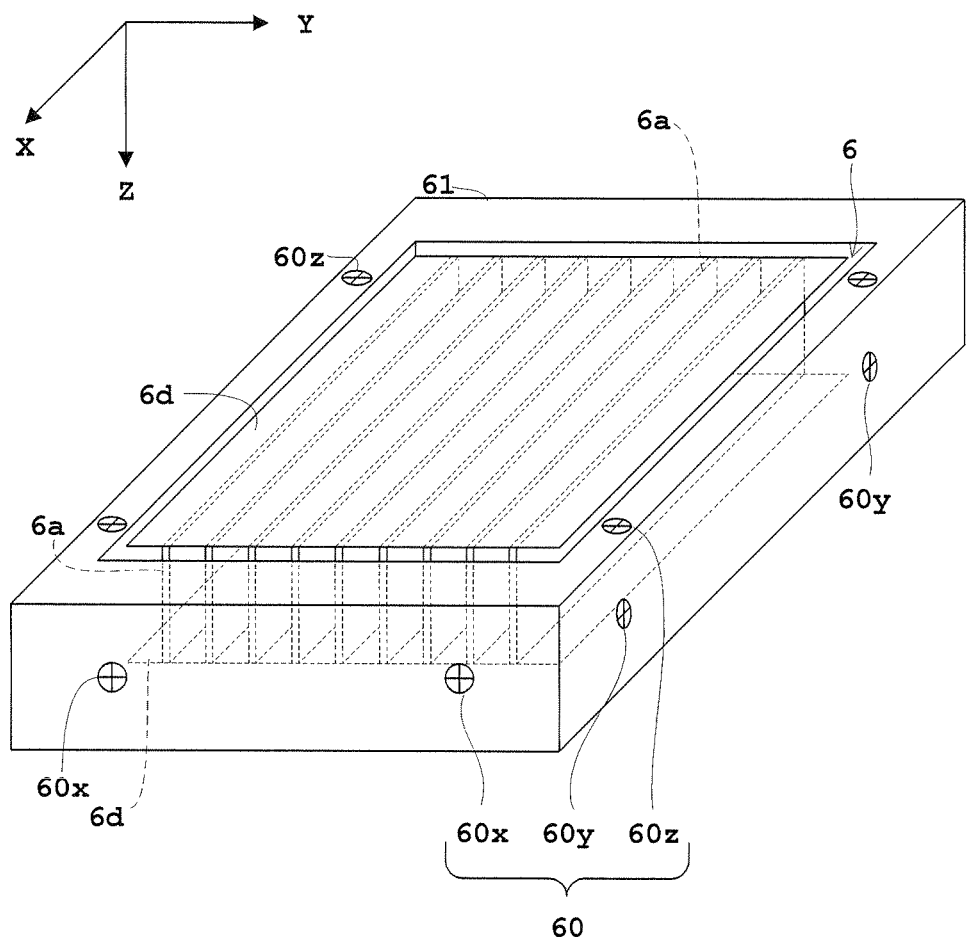
FIG. 7 is a perspective view showing an outline of a moving mechanism for moving the grid in varied directions.

An embodiment of this invention will be described hereinafter with reference to the drawings. FIG. 1 is a block diagram of an X-ray imaging apparatus according to the embodiment. FIG. 2 is a schematic view of a detecting plane of a flat panel X-ray detector (FPD). FIG. 3 is a schematic view of a common grid. FIG. 4 is a schematic view of the grid with marking absorbers. FIG. 4 (a) is a perspective view showing an overall outline of the grid, FPD and marking absorbers along with an X-ray tube, FIG. 4 (b) is an enlarged view of the marking absorbers and adjacent components, and FIG. 4 (c) is a sectional view seen from arrow A of FIG. 4 (b). FIG. 5 is a schematic plan view illustrating an effective field of view area of the FPD. FIG. 6 is a schematic view showing a plurality of pixels centering on shadowed pixels. FIG. 7 is a perspective view showing an outline of a moving mechanism for moving the grid in varied directions. This embodiment will be described taking X-rays as an example of radiation.

As shown in FIG. 1, the X-ray imaging apparatus according to this invention includes a top board 1 for supporting a subject M, an X-ray tube 2 for emitting X-rays toward the subject M, a flat panel X-ray detector (hereinafter abbreviated as "FPD") 3 for detecting the X-rays emitted from the X-ray tube 2 and transmitted through the subject M, an image processor 4 for carrying out image processes based on the X-rays detected by the FPD 3, and a display 5 for displaying X-ray images having undergone the image processes by the image processor 4. The display 5 is in the form of a display device such as a monitor, television or the like. A grid 6 is attached to the detecting plane of the FPD 3. In addition, a moving mechanism 60 (see FIG. 7) for moving the grid 6 in varied directions is arranged on each surface of an outer frame 61 (see FIG. 7) enclosing the grid 6. The X-ray tube 2 corresponds to the radiation emitting device in this invention. The flat panel X-ray detector (FPD) 3 corresponds to the radiation detecting device and the shadow pixel detecting device in this invention. The grid 6 corresponds to the scattered radiation removing device in this invention. The moving mechanism 60 corresponds to the moving device in this invention.

The image processor 4 includes a central processing unit (CPU) and others. The programs and the like for carrying out various image processes are written and stored in a storage medium represented by a ROM (Read-only Memory). The CPU of the image processor 4 reads from the storage medium and executes the programs and the like to carry out image processes corresponding to the programs. In particular, a first intensity estimating unit 41, a shadow position calculating unit 42, a focal position calculating unit 43, a correcting unit 44, a parameter proofing unit 45, a pixel specifying unit 51, a transmittance calculating unit 52, a transmittance interpolating unit 53, a second intensity estimating unit 54, an intensity interpolating unit 55, a rate of change calculating unit 56 and a rate of change interpolating unit 57, described hereinafter, of the image processor 4 execute programs relating to calculation of shadow positions, calculation of a focal position, correction and proofing of parameters (direct ray transmittances and transmission scattered ray intensities), specification of certain pixels, calculation and interpolation of direct ray transmittances, intensity estimation and interpolation, and calculation of rates of change. In this way, the above components carry out calculation of the shadow positions, calculation of the focal position, correction and proofing of the parameters, specification of the certain pixels, calculation and interpolation of the direct ray transmittances, intensity estimation and interpolation, and calculation and interpolation of the rates of change, corresponding to the programs, respectively.

The image processor 4 includes the first intensity estimating unit 41 for estimating intensity in the presence of a subject M on the assumption that pixels with shadows falling on at least part thereof are free from the shadows, the shadow position calculating unit 42 for calculating the shadow positions, the focal position calculating unit 43 for calculating the focal position, the correcting unit 44 for correcting physical quantities (parameters) relating to intensity as described hereinafter, the parameter proofing unit 45 for proofing the parameters also as described hereinafter, the pixel specifying unit 51 for specifying certain pixels, the transmittance calculating unit 52 for calculating direct ray transmittances, the transmittance interpolating unit 53 for interpolating the direct ray transmittances, the second intensity estimating unit 54 for estimating intensities (transmission scattered ray intensities and estimated direct ray intensities), the intensity interpolating unit 55 for interpolating the intensities, the rate of change calculating unit 56 for calculating rates of change, and the rate of change interpolating unit 57 for interpolating the rates of change. The correcting unit 44 corresponds to the correcting device in this invention. The transmittance calculating unit 52 and transmittance interpolating unit 53, and the rate of change calculating unit 56 and rate of change interpolating unit 57 correspond to the physical quantity calculating device in this invention.

As shown in FIG. 2, the FPD 3 has a plurality of detecting elements d sensitive to X-rays arranged in a two-dimensional matrix form on the detecting plane thereof. The detecting elements d detect X-rays by converting the X-rays transmitted through the subject M into electric signals to be stored once, and reading the electric signals stored. The electric signal detected by each detecting element d is converted into a pixel value corresponding to the electric signal. An X-ray image is outputted by allotting the pixel values to pixels corresponding to positions of the detecting elements d. The X-ray image is fed to the first intensity estimating unit 41, shadow position calculating unit 42, pixel specifying unit 51, transmittance calculating unit 52 and second intensity estimating unit 54 of the image processor 4 (see FIGS. 1 and 8). Thus, the FPD 3 has the plurality of detecting elements d arranged in rows and columns (two-dimensional matrix form) for detecting X-rays. The detecting elements d correspond to the detecting elements in this invention.

As shown in FIG. 3, the common grid 6 has, arranged alternately, absorbing foil strips 6a for absorbing scattered rays (scattered X-rays), and intermediate layers 6c for transmitting scattered rays through. The absorbing foil strips 6a and intermediate layers 6c are covered by grid covers 6d located on an X-ray incidence plane and on an opposite plane with the absorbing foil strips 6a and intermediate layers 6c in between. In order to clarify illustration of the absorbing foil strips 6a, the grid covers 6d are shown in two-dot chain lines, and other details of the grid 6 (e.g. a structure for supporting the absorbing foil strips 6a) are not shown. The absorbing foil strips 6a correspond to the absorbing layers in this invention.

The absorbing foil strips 6a and intermediate layers 6c extending in an X-direction in FIG. 3 are arranged alternately in order in a Y-direction in FIG. 3. The X-direction in FIG. 3 is parallel to the direction of columns of the detecting elements d of FPD 3 (see FIG. 2), while the Y-direction in FIG. 3 is parallel to the direction of rows of the detecting elements d of FPD 3 (see FIG. 2). Therefore, the direction of arrangement of the absorbing foil strips 6a is parallel to the rows of the detecting elements d. Thus, the direction of arrangement of the absorbing foil strips 6a corresponds to the Y-direction, and the longitudinal direction of the absorbing foil strips 6a corresponds to the X-direction. To summarize the above, the direction of arrangement of the absorbing foil strips 6a (Y-direction) is parallel to the direction of the rows, of the direction of rows and the direction of columns of the detecting elements d. As shown in FIG. 3, the grid 6 is constructed by arranging each of the absorbing foil strips 6a parallel to the detecting plane of the FPD 3.

As the absorbing foil strips 6a absorb X-rays, shadows 32 of the absorbing foil strips 6a (see FIGS. 4 and 6) appear on the FPD 3. The intervals between the absorbing foil strips 6a are adjusted so that the shadows 32 may be cyclically projected to every two or more pixels (four pixels in this embodiment). Where the intervals between the pixels (pixel pitch) are Wd, the grid 6 is constructed to have the intervals between the absorbing foil strips 6a larger than the intervals Wd between the pixels.

The intermediate layers 6c are void. Therefore, the grid 6 is also an air grid. The absorbing foil strips 6a are not limited to any particular material, as long as a material such as lead is used which absorbs radiation represented by X-rays. As the intermediate layers 6c, instead of being void as noted above, any intermediate material such as aluminum or organic substance may be used which transmits radiation represented by X-rays.

In this embodiment, as shown in FIGS. 4 (a)-(c), marking absorbers 7 are separately provided to assure that the widths of shadows in the direction of arrangement (Y-direction) of the absorbing foil strips 6a are at least equal to the width of one pixel. By forming such marking absorbers 7, the grid 6 is constructed to have the widths in the direction of arrangement of certain of the absorbing foil strips 6a including the absorbers 7 larger than the intervals between the respective pixels.

In this embodiment, the marking absorbers 7 are arranged in end regions inside an effective field of view area 3A of the FPD 3 (see FIGS. 4 (a) and 5). Further, as shown in FIG. 4 (a), the marking absorbers 7 are provided in areas including a perpendicular PL from the focus F of the X-ray tube 2 to the FPD 3. Therefore, in order to provide the marking absorbers 7 in the end regions inside the effective field of view area 3A of the FPD 3 and in the areas including the perpendicular PL, an X-ray irradiation field from the X-ray tube 2 is controlled and respective positions of the X-ray tube 2, FPD 3 and grid 6 are set so that locations at which the perpendicular PL and FPD 3 intersect be in the end regions inside the effective field of view area 3A.

As shown in FIGS. 4 (b) and (c), the marking absorbers 7 include an upper left absorber 71 attached to an upper part of a left surface of an absorbing foil strip 6a, and a lower right absorber 72 attached to a lower part of a lower right surface of the absorbing foil strip 6a. Sign 31 is affixed to each pixel forming the X-ray image, sign 32 is affixed to the shadows formed by the absorbing foil strips 6a, and sign 33 is affixed to the shadows of the upper left absorber 71, the lower right absorber 72 and the absorbing foil strip 6a having these absorbers 71 and 72 attached thereto (hereinafter abbreviated as "shadows of the marking absorbers 7"). The marking absorbers 7 are provided so that zones where the width of the shadows 33 is at least equal to one pixel be formed over at least two pixels along the length of the shadows 32 and 33 in the longitudinal direction (X-direction). The length in the longitudinal direction of the marking absorbers 7 (upper left absorber 71 and lower right absorber 72) is represented by Lg.

As shown in FIG. 4 (a), the distance of the X-ray tube 2 to the FPD 3 in the direction of the perpendicular PL (SID: Source Image Distance) is represented by L. As shown in FIGS. 4 (b) and 4 (c), the width (thickness) of the absorbing foil strips 6a is represented by t, the height of the absorbing foil strips 6a by h, the distance between the absorbing foil strips 6 and FPD 3 by d, the pixel pitch by Wd as described in FIG. 3, the width of the shadows 33 by Wg, the height of the upper left absorber 71 and lower right absorber 72 by H, and the width of the upper left absorber 71 and lower right absorber 72 by W.

In this embodiment, the SID (L) serving as the reference is set to 1000 mm, the width of the shadows 32 repeated in cycles, rather than the shadows 33 of the marking absorbers 7, is set to 0.6 mm, and the pixel pitch Wd=0.15 mm. Therefore, when the shadow centers of the absorbing foil strips 6a are adjusted to the pixel centers, the shadows 32 of the absorbing foil strips 6a will fall on every four pixels. When the width W of the upper left absorber 71 and lower right absorber 72=0.1 mm, the height H of the upper left absorber 71 and lower right absorber 72=1 mm, and the length Lg in the longitudinal direction of the marking absorbers 7 (upper left absorber 71 and lower right absorber 72)=2 mm, an overlap of the shadow 33 of the marking absorbers 7 and the shadow 32 of the absorbing foil strip 6a can be prevented. This facilitates calculation of the shadow positions by the shadow position calculating unit 42 to be described hereinafter. Further, as shown in FIGS. 4 (a) and 5, the marking absorbers 7 are provided in the end regions inside the effective field of view area 3A of the FPD 3, and hence hardly any influence on X-ray images of the subject M. Since the marking absorbers 7 are provided in areas including the perpendicular PL as shown in FIG. 4 (a), even if the SID changes, there occurs hardly any change in shadow positions in the locations where the marking absorbers 7 are provided. This allows shadow pixels under observation to be limited to a narrow range such as pixel columns (a, b, c, d, e, f and g) to be described hereinafter.

The SID (L) at the time of X-ray imaging in this embodiment changes in a range of L=900 mm to 1100 mm, the reference SID is set to L=1000 mm, and the grid 6 is manufactured to have the absorbing foil strips 6a with a convergence condition also set according to SID (L)=1000 mm. The distance d between the absorbing foil strips 6 and FPD 3 is set to 20 mm, the height h of the absorbing foil strips 6a is set to 5.7 mm, and the thickness t of the absorbing foil strip 6a is set to 0.03 mm. In the case of such design conditions for the absorbing foil strips 6a, the width Wg of the shadows 33, under all imaging conditions, that is even when L=1100 mm which is the smallest in the range of SID (L)=900 mm to 1100 mm, Wg=0.235 mm is derived from a simple geometric calculation, and thus Wg is at least equal to the pixel pitch Wd=0.15 mm. Therefore, even when SID is as long as L=1100 mm, the width Wg of the shadows 33 of the marking absorbers 7 never becomes narrower than the pixel pitch Wd, which would otherwise make it impossible to determine shadow positions. The marking absorbers 7 are provided so that Wg of the shadows 33 does not exceed a width of two pixels (2×Wd=0.3 mm), which can reduce the number of pixels influenced by the shadows 33 of the marking absorbers 7.

Further, the length Lg in the longitudinal direction of the marking absorbers 7 (upper left absorber 71 and lower right absorber 72) is 2 mm, which is at least equal to a two-pixel range, i.e. 2×Wd=0.3 mm, also in the longitudinal direction. Thus, the marking absorbers 7 are provided so that a zone where the width of the shadow 33 is at least equal to one pixel is formed over at least two pixels along the length of the shadows 32 and 33 in the longitudinal direction (X-direction). As shown in FIG. 6, the number of the pixels in the longitudinal direction (X-direction) on which the shadows 33 of the marking absorbers 7 fall is set to 13. Variable factors such as statistical errors can be decreased by obtaining an average intensity of the 13 pixels along the longitudinal direction.

A plurality of pixels centering on a pixel column on which the shadows 33 of the marking absorbers 7 fall are set to 7 pixels widthwise (Y-direction, i.e. the direction of arrangement of the absorbing foil strips 6a)×13 pixels lengthwise (X-direction, i.e. the longitudinal direction). The FPD 3 has a function (that is, a shadow pixel detecting function) to detect also the X-ray intensities of shadow pixels 34 consisting of the 7 pixels widthwise×13 pixels lengthwise (see the bold-line frame in FIG. 6). Since the FPD 3 has also the shadow pixel detecting function in this embodiment as noted above, there is no need to provide separately a detector for detecting shadow positions of the marking absorbers 7. In FIG. 6, the pixel columns which form a target of shadow pixel detection are, in order from left, a, b, c, d, e, f, and g. As noted hereinbefore, the shadows 32 of the absorbing foil strips 6a fall on every four pixels. Therefore, as seen also from FIG. 6, the shadow 32 of an absorbing foil strip 6a falls on a pixel column adjoining on the left of the pixel column a at the left end of the shadow pixels 34 and, conversely, the shadow 32 of an absorbing foil strip 6a falls on a pixel column adjoining on the right of the pixel column g at the right end of the shadow pixels 34. Therefore, the shadow pixels 34 may be selected to be pixels which include the shadows 33 of the marking absorbers 7, and do not include the next shadows 32.

When the intermediate layers 6c are not void but are formed of an intermediate material, the intermediate layers 6c may be dented only where the marking absorbers 7 are provided, and the marking absorbers 7 (e.g. the upper left absorbers 71 and lower right absorbers 72) may be fitted in the dented portions. Further, only the intermediate layers 6c having the marking absorbers 7 provided therein may be void, and the other intermediate layers 6c may be formed of the intermediate material.

As shown in FIG. 7, the moving mechanism 60 is provided around the grid 6 for moving the grid 6 in all directions. The moving mechanism 60 is arranged on each surface of the outer frame 61 surrounding the grid 6. The grid covers 6d covering the absorbing foil strips 6a and intermediate layers 6c (see FIG. 3) are constructed fine-tunable relative to the outer frame 61, and are movable in all directions while being supported by the moving mechanism 60 provided on each surface of the outer frame 61. Specifically, the moving mechanism 60 includes X-direction adjust screws 60x for fine-tuning and moving the grid 6 with the absorbing foil strips 6a and grid covers 6d parallel to the longitudinal direction (X-direction) of the absorbing foil strips 6a, Y-direction adjust screws 60y for fine-tuning and moving the grid 6 with the absorbing foil strips 6a and grid covers 6d parallel to the direction of arrangement (Y-direction) of the absorbing foil strips 6a, and Z-direction adjust screws 60z for fine-tuning and moving the grid 6 with the absorbing foil strips 6a and grid covers 6d up and down parallel to the vertical direction (Z-direction).

In response to the directions in which the respective screws 60x, 60y and 60z are turned, the absorbing foil strips 6a and grid covers 6d supported at the forward ends of the screws move, whereby the entire grid 6 moves with the absorbing foil strips 6a and grid covers 6d. When, for example, the X-direction adjust screws 60x are turned in the right screw direction, the grid 6 will move in the depth direction along the X-direction. When the Y-direction adjust screws 60z are turned in the right screw direction, the grid 6 will move leftward in FIG. 7 along the Y-direction. When the Z-direction adjust screws 60z are turned in the right screw direction, the grid 6 will descend downward along the Z-direction. While FIG. 7 shows the grid covers 6d being present only inwardly of the outer frame 61 in order to clarify illustration thereof, it should be noted that the grid covers 6d actually extend to the forward ends of the threads of the Z-direction adjust screws 60z. Moving distances of the grid 6 are determined by turning angles of the screws. Therefore, in order to move the grid 6 a predetermined distance, the screws are turned by the angle corresponding to the predetermined distance. In this embodiment, the Y-direction adjust screws 60y are turned right and left to move the grid 6 parallel to the direction of arrangement (Y-direction) of the absorbing foil strips 6a only by an integral multiple (e.g. m=2 when the integer is m) of each pixel pitch Wd (see FIGS. 3 and 4 (c)).

Figure 8:
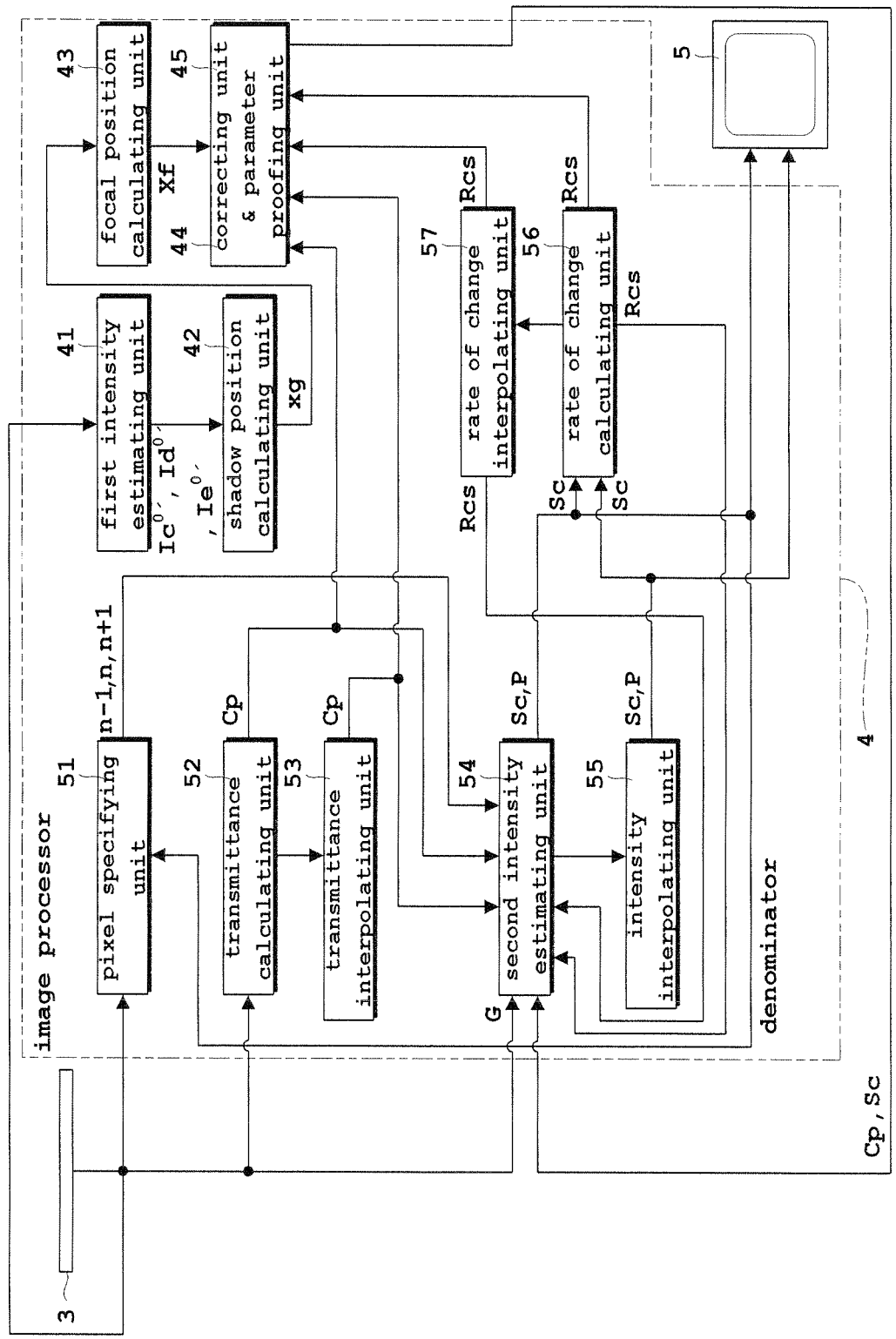
FIG. 8 is a block diagram showing a specific construction of an image processor and data flows according to the embodiment.
Figure 9:
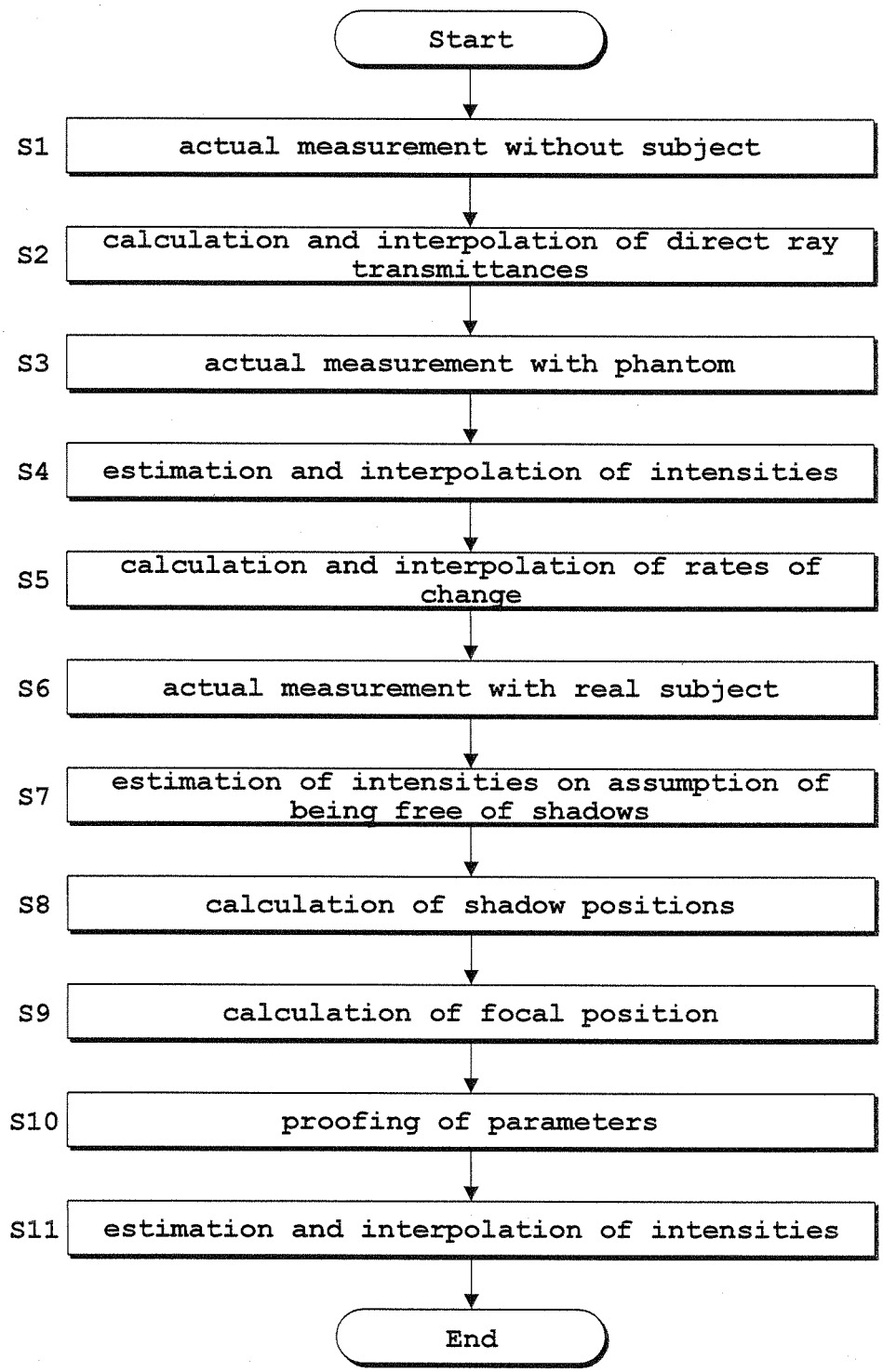
FIG. 9 is a flow chart showing a sequence of X-ray imaging according to the embodiment.
Figure 10:
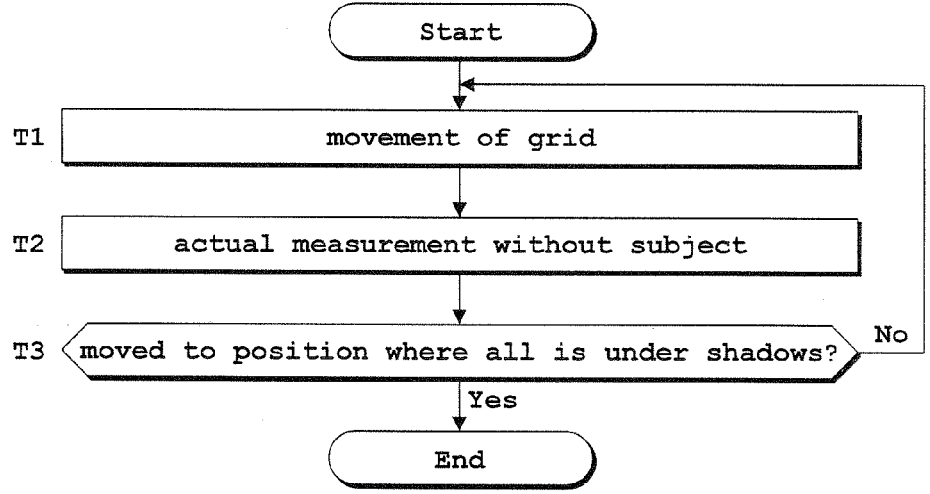
FIG. 10 is a flow chart showing a sequence of actual measurement of a relationship between X-ray intensity and reference position.
Figure 11:
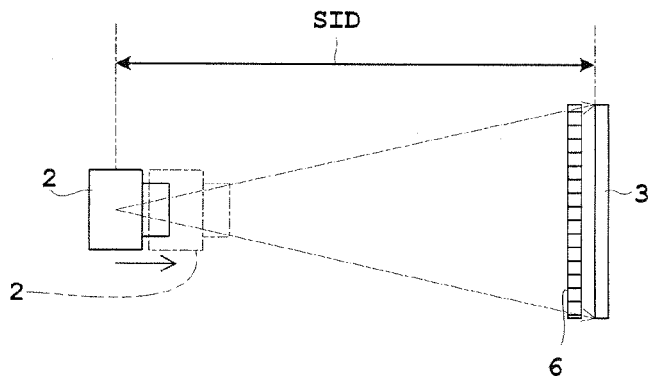
FIG. 11 is a view schematically showing X-ray imaging without a subject.
Figure 12:
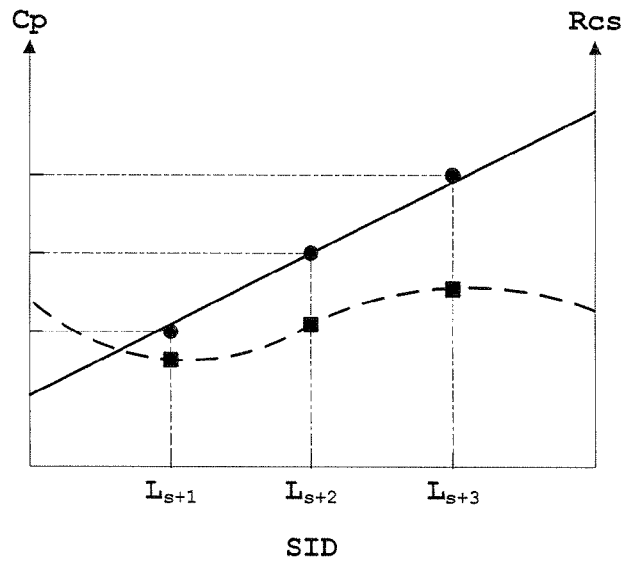
FIG. 12 is a graph schematically showing a relationship between SID, direct X-ray transmittance and rate of change of transmission scattered ray intensity.
Figure 13:
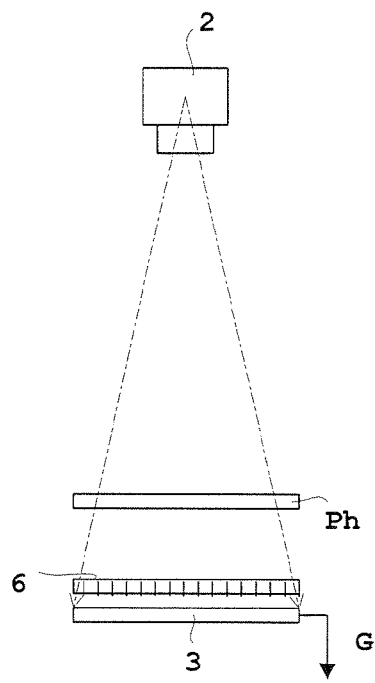
FIG. 13 is a view schematically showing X-ray imaging in the presence of a subject, using a phantom in the form of an acrylic plate as the subject.
Figure 14:
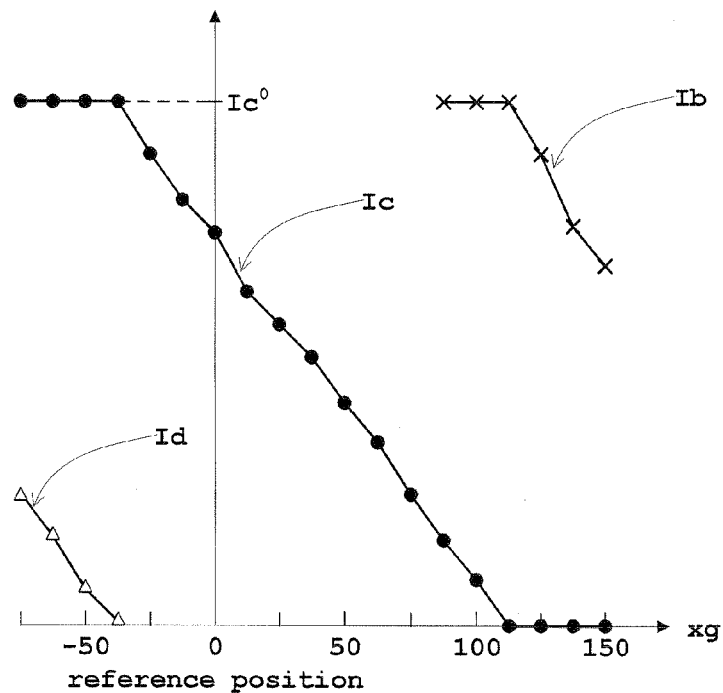
FIG. 14 is a graph of a relationship between X-ray intensity and shadow position.
Figure 15:
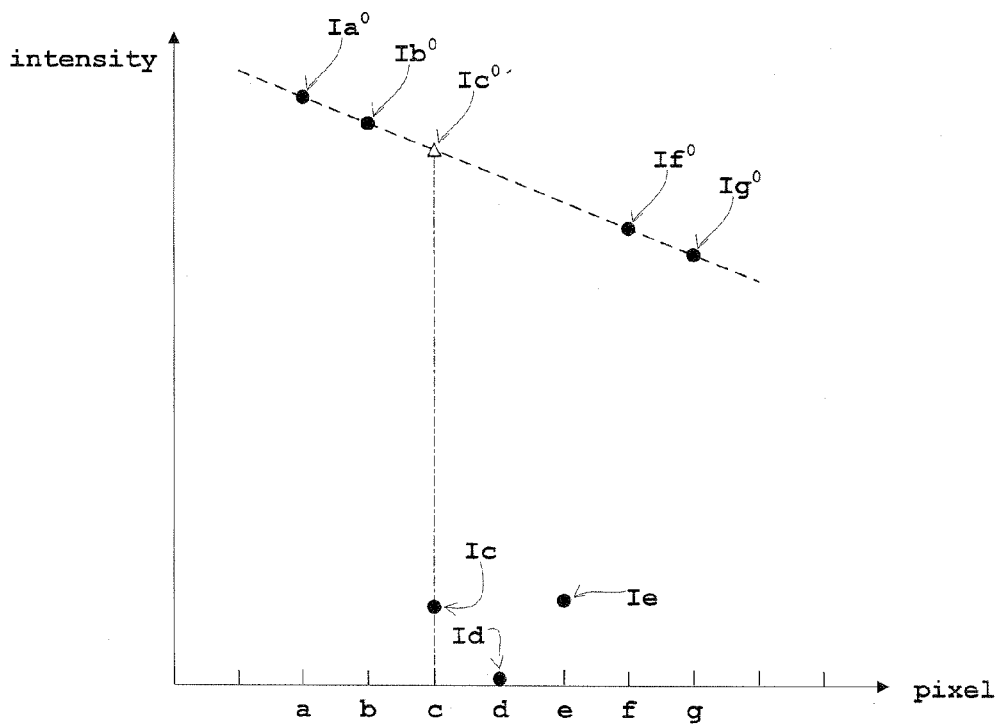
FIG. 15 is a graph of shadow pixels and actual measurement results of intensity used for estimation of intensity assuming a shadow-free state.
Figure 16:
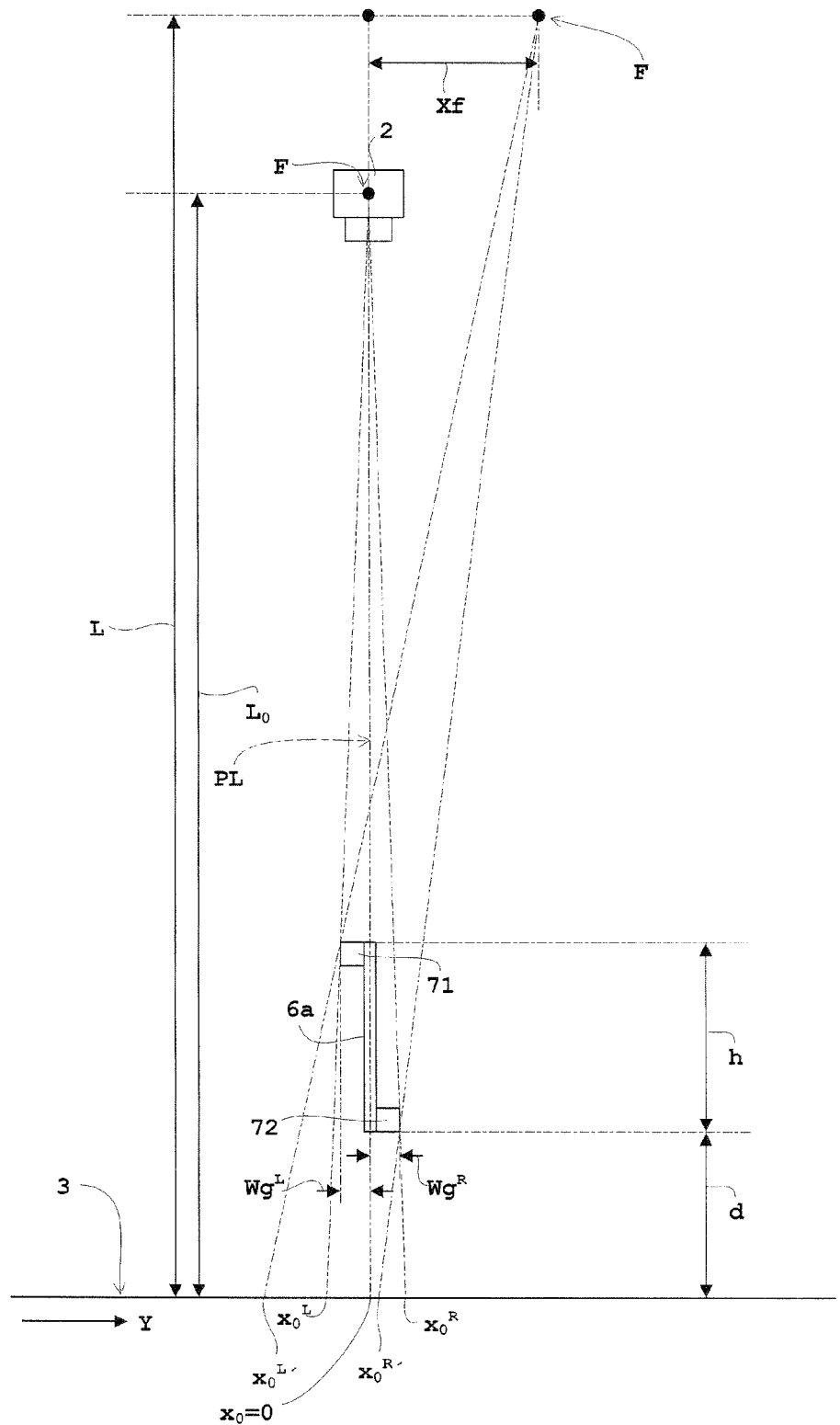
FIG. 16 is a side view schematically showing a relationship between each shadow position and focal position used to determine a focal position.
Figure 17:
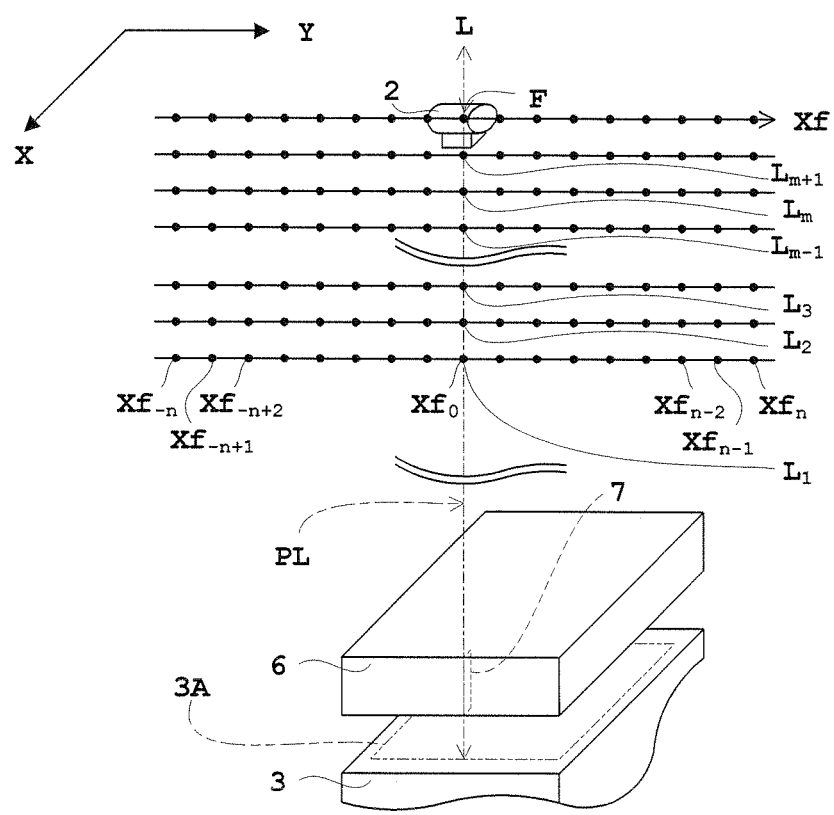
FIG. 17 is a view schematically showing a positional relationship of a discrete focal position to each discrete SID.
Figure 18:
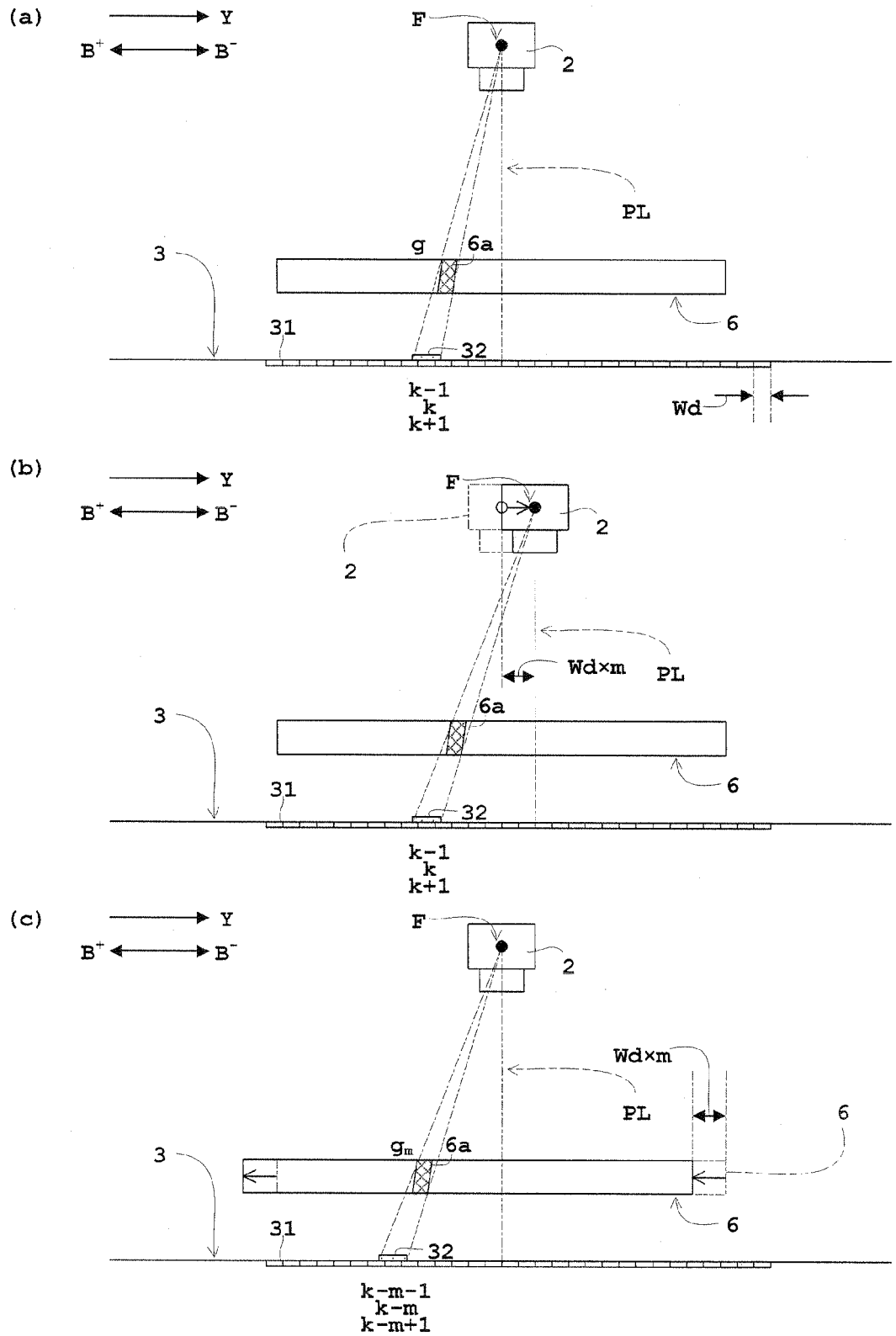
FIG. 18 is a side view schematically showing a positional relationship between absorbing foil strips of the grid and shadow positions.

An actual X-ray imaging and data flows according to this embodiment will be described with reference to FIGS. 8 through 18. FIG. 8 is a block diagram showing a specific construction of an image processor and data flows. FIG. 9 is a flow chart showing a sequence of X-ray imaging. FIG. 10 is a flow chart showing a sequence of actual measurement of a relationship between X-ray intensity and reference position. FIG. 11 is a view schematically showing X-ray imaging without a subject. FIG. 12 is a graph schematically showing a relationship between SID, direct X-ray transmittance and rate of change of transmission scattered ray intensity. FIG. 13 is a view schematically showing X-ray imaging in the presence of a subject, using a phantom in the form of an acrylic plate as the subject. FIG. 14 is a graph of a relationship between X-ray intensity and shadow position. FIG. 15 is a graph of shadow pixels and actual measurement results of intensity used for estimation of intensity assuming a shadow-free state. FIG. 16 is a side view schematically showing a relationship between each shadow position and focal position used to determine a focal position. FIG. 17 is a view schematically showing a positional relationship of a discrete focal position to each discrete SID. FIG. 18 is a side view schematically showing a positional relationship between absorbing foil strips of the grid and shadow positions.

As shown in FIG. 8, the FPD 3 detects X-ray intensities of a plurality of pixels centering on the pixels coming under the shadows 33 of the marking absorbers 7. In this embodiment, as described above, X-ray intensities of the shadow pixels 34 consisting of 7 pixels widthwise×13 pixels lengthwise shown in FIG. 6 are detected. Based on the X-ray intensities of the plurality of pixels (a, b, f and g in FIG. 6 here) around the pixels coming under the shadows 33, which are obtained by the FPD 3 through actual measurement in the presence of the subject M used in X-ray imaging, the first intensity estimating unit 41 estimates intensity in the presence of the subject M on the assumption that the pixel columns (c, d and e in FIG. 6 here) with the shadows 33 falling on at least part thereof are free of the shadows. In this embodiment, the pixel columns free of the shadow 33 are a, b, f and g, and assuming that average intensities of the X-ray intensities along the longitudinal direction of these pixel columns are $Ia^o$, $Ib^o$, $If^o$ and $Ig^o$, respectively, and that average intensities of the X-ray intensities along the longitudinal direction of the pixel columns c, d and e with the shadows 33 falling on at least part thereof are Ic, Id and Ie, respectively, the first intensity estimating unit 41, based on the X-ray intensities (average intensities here) $Ia^o$, $Ib^o$, $If^o$ and $Ig^o$ of the pixel columns a, b, f and g around the pixels under the shadows 33, estimates intensities of the pixel columns c, d and e which are at least partly under the shadows 33, that is on the assumption that the shadows 33 do not fall on the pixel columns c, d, and e having X-ray intensities (average intensities here) Ic, Id and Ie. These estimated intensities are fed to the shadow position calculating unit 42 as $Ic^{o'}$, $Id^{o'}$ and $Ie^{o'}$, respectively.

The shadow position calculating unit 42 calculates shadow positions in the presence of the subject M, based on (A), (B) and (C) described below. That is, (A) is the X-ray intensities of the pixels at least partly under the shadows obtained through actual measurement by the FPD 3 in the presence of the subject M. (B) is the X-ray intensities $Ic^{o'}$, $Id^{o'}$ and $Ie^{o'}$ estimated by the first intensity estimating unit 41. (C) is, as shown in FIG. 14, a relationship between X-ray intensities of the pixel columns (c, d and e in FIG. 6 here) at least partly under the shadows 33 in the absence of the subject and shadow positions corresponding thereto. The relationship between the X-ray intensities and shadow positions in FIG. 14 will be described hereinafter. The shadow positions (indicated "xg" in FIG. 8) in the presence of the subject M calculated by the shadow position calculating unit 42 are fed to the focal position calculating unit 43.

The focal position calculating unit 43 calculates a focal position of the FPD 3 relative to the X-ray tube 2 in the presence of the subject M, based on (a), (b) and (c) described below. That is, (a) is the shadow positions xg in the presence of the subject M calculated by the shadow position calculating unit 42. (b) is the distance d between the absorbing foil strips 6 and FPD 3. (c) is the shadow positions xg relative to a reference position with the perpendicular PL extending from the focus F of the X-ray tube 2 to the FPD 3 in the absence of the subject M. The focal position calculating unit 43 calculates the focal position (indicated "Xf" in FIG. 8) of the FPD 3 relative to the X-ray tube 2 in the presence of the subject M by geometric calculation using (a); (b) and (c), and feeds it to the parameter proofing unit 45.

The correcting unit 44 corrects direct ray transmittances and rates of change relating to transmission scattered ray intensities as physical quantities (parameters) relating to intensity as follows. That is, the correcting unit 44 corrects the direct ray transmittances and rates of change based on an assumption that the focal position of the X-ray tube 2 has moved in the direction (Y-direction) opposite to a direction of movement (Y-direction which is the direction of arrangement of the absorbing foil strips 6a) caused by the Y-direction adjust screws 60y (see FIG. 7) of the moving mechanism 60. Specifically, X-rays are emitted from the X-ray tube 2 in a state where the grid 6 has been moved a predetermined distance by the Y-direction adjust screws 60y of the moving mechanism 60, and the correcting unit 44 corrects the direct ray transmittances (indicated "Cp" in FIG. 8) calculated or interpolated by the transmittance calculating unit 52 or transmittance interpolating unit 53, and the rates of change (indicated "Rcs" in FIG. 8) relating to the transmission scattered ray intensities (indicated "Sc" in FIG. 8) calculated or interpolated by the rate of change calculating unit 56 or rate of change interpolating unit 57. The direct ray transmittances and the rates of change corrected by the correcting unit 44 are used to create relationships between physical quantities calculated before an X-ray imaging shown in FIG. 17 to be described hereinafter, and focal positions of the X-ray tube 2 relative to the FPD 3 matched therewith (positional relationship of a discrete focal position to each discrete SID).

The parameter proofing unit 45, based on (α) and (β) described below, proofs the direct ray transmittances and the rates of change relating to transmission scattered ray intensities as physical quantities (parameters) relating to X-ray intensity at the time of X-ray imaging. That is, (α) is a relationship between physical quantities (direct ray transmittances and rates of change relating to transmission scattered ray intensities here) obtained before X-ray imaging and the focal position of the X-ray tube 2 relative to the FPD 3 matched therewith. (β) is the focal position Xf calculated by the focal position calculating unit 43. The direct ray transmittances (indicated "Cp" in FIG. 8) and the rates of change (indicated "Rcs" in FIG. 8) relating to the transmission scattered ray intensities (indicated "Sc" in FIG. 8) proofed by the parameter proofing unit 45 are fed to the second intensity estimating unit 54.

On the other hand, the pixel specifying unit 51 specifies certain pixels among the pixels forming an X-ray image. In this embodiment, the pixel specifying unit 51 specifies a combination of three pixels consisting of an (n−1)th pixel, an adjoining, nth pixel and a next adjoining, (n+1)th pixel (indicated "n−1", "n" and "n+1" in FIG. 8), and feeds the combination to the second intensity estimating unit 54. When the absolute value of the denominator included in the solution of simultaneous equations described hereinafter has a predetermined value or less (the denominator being "0" in this embodiment), the pixel specifying unit 51 does not select the pixels forming the combination for the simultaneous equations, but selects and specifies other pixels for the combination. Since the simultaneous equations are derived from the second intensity estimating unit 54 as is clear from the description made hereinafter, data relating to the denominator (indicated "denominator" in FIG. 8) derived from the second intensity estimating unit 54 is fed to the pixel specifying unit 51.

The transmittance calculating unit 52 determines, in relation to discrete SIDs, direct ray transmittances Cp which are transmittance ratios between direct rays (direct X-rays) before transmission and after transmission through the grid 6 obtained from actual measurements taken in the absence of a subject. In this embodiment, the transmittance calculating unit 52 calculates the direct ray transmittances Cp, and feeds them to the parameter proofing unit 45, transmittance interpolating unit 53 and second intensity estimating unit 54.

The transmittance interpolating unit 53 interpolates the direct ray transmittances Cp calculated by the transmittance calculating unit 52 in SIDs around the above discrete is SIDs. The interpolated direct ray transmittances Cp also are fed to the parameter proofing unit 45 and second intensity estimating unit 54.

The second intensity estimating unit 54 estimates scattered ray intensities (scattered X-ray intensities) at the predetermined pixels specified by the pixel specifying unit 51, and direct ray intensities (direct X-ray intensities) at the predetermined pixels. In this embodiment, before X-ray imaging, based on the direct ray transmittances Cp calculated by the transmittance calculating unit 52, or the direct ray transmittances Cp interpolated by the transmittance interpolating unit 53, and actual measurement intensities (indicated "G" in FIG. 8) which are intensities after transmission through the grid 6 in an actual measurement taken in the presence of a subject M (which is a phantom here), the second intensity estimating unit 54 estimates transmission scattered ray intensities Sc and estimated direct ray intensities (indicated "P" in FIG. 8) which are direct ray intensities before transmission through the grid 6, and feeds them to the intensity interpolating unit 55, rate of change calculating unit 56 and display 5. At the time of X-ray imaging, estimated direct ray intensities P are estimated based on the direct ray transmittances Cp calculated by the transmittance calculating unit 52 or the direct ray transmittances Cp interpolated by the transmittance interpolating unit 53 or the direct ray transmittances Cp proofed by the parameter proofing unit 45, and the rates of change Rcs calculated by the rate of change calculating unit 56, the rates of change Rcs interpolated by the rate of change interpolating unit 57 or the rates of change Rcs proofed by the parameter proofing unit 45, and the actual measurement intensities G. In this embodiment, the second intensity estimating unit 54 estimates the transmission scattered ray intensities Sc and estimated direct ray intensities P by solving the simultaneous equations, and therefore data "denominator" relating to the denominator included in the solution is also obtained, and feeds the data "denominator" relating to the denominator to the pixel specifying unit 51.

The intensity interpolating unit 55 interpolates the scattered ray intensities (scattered X-ray intensities) at the predetermined pixels and the direct ray intensities (direct X-ray intensities) at the predetermined pixels estimated by the second intensity estimating unit 54. In this embodiment, the intensity interpolating unit 55 interpolates the transmission scattered ray intensities Sc or the estimated direct ray intensities P estimated by the second intensity estimating unit 54, and feeds them to the rate of change calculating unit 56 and display 5.

Using the intensities estimated by the second intensity estimating unit 54 based on the actual measurement in the presence of a subject M, the rate of change calculating unit 56 calculates a value of each pixel from an average value or smoothing and interpolating calculations, as reference intensity about all the pixels relating to the intensities, and calculates a rate of change of each pixel relative to the calculated value. This is reflected in the X-ray imaging of different subjects M, using the rates of change Rcs calculated by the rate of change calculating unit 56, or the rates of change interpolated by the rate of change interpolating unit 57. In this embodiment, the rates of change Rcs are calculated, at the time of X-ray imaging, using the transmission scattered ray intensities Sc estimated by the second intensity estimating unit 54 and the transmission scattered ray intensities Sc interpolated by the intensity interpolating unit 55, and are fed to the second intensity estimating unit 54 again.

In this embodiment, an actual X-ray imaging follows a procedure as shown in FIG. 9.

(Step S1) Actual Measurement without Subject

X-ray imaging is carried out in the absence of a subject. As shown in FIG. 11, X-rays are emitted from the X-ray tube 2 toward the grid 6 and FPD 3 with no subject interposed between the X-ray tube 2 and grid 6, thereby to carry out X-ray imaging for actual measurement without a subject. That is, the X-ray tube 2 emits X-rays in the absence of a subject, to be incident on the FPD 3 through the grid 6, thereby obtaining actual measurement data without a subject. Specifically, the detecting elements d of the FPD 3 (see FIG. 3) read the X-rays as converted to electric signals without a subject, and provide pixel values corresponding to the electric signals.

(Step S2) Calculation and Interpolation of Direct Ray Transmittances

The pixel values are equivalent to the intensities after transmission through the grid 6 which are obtained by actual measurement without a subject. On the other hand, the intensity before transmission through the grid 6 is known. Therefore, the direct ray transmittances Cp, which are transmittances of the (pre-transmission) intensity before transmission through the grid 6 and the (post-transmission) intensities after transmission through the grid 6, are expressed by ratios between the intensity before transmission through the grid 6 and the intensities after transmission through the grid 6 (that is, the pixel values detected by the FPD 3).

Thus, the intensities after transmission through the grid 6 which are equivalent to the pixel values obtained from the FPD 3 and the known intensity before transmission through the grid 6 are fed to the transmittance calculating unit 52. The transmittance calculating unit 52 calculates the direct ray transmittances Cp expressed by the ratios between the intensity before transmission and the intensities after transmission through the grid 6. The transmittance calculating unit 52 calculates such direct ray transmittances Cp with respect to the discrete SIDs.

The SID varies in actual X-ray imaging as shown in FIG. 11. Then, X-ray imaging is carried out similarly without a subject, and the transmittance calculating unit 52 obtains a direct ray transmittance Cp for each of discrete distances $L_{s+1}, L_{s+2}, L_{s+3}$ and so on as shown in black dots in FIG. 12. The direct ray transmittances Cp for the discrete distances $L_{s+1}, L_{s+2}, L_{s+3}$ and so on are fed to the parameter proofing unit 45, transmittance interpolating unit 53 and second intensity estimating unit 54. The transmittance calculating unit 52 obtains a direct ray transmittance Cp for each pixel also, and feeds it to the parameter proofing unit 45, transmittance interpolating unit 53 and second intensity estimating unit 54.

The transmittance interpolating unit 53 interpolates the direct ray transmittances Cp calculated by the transmittance calculating unit 52 in distances around the discrete distances $L_{s+1}, L_{s+2}, L_{s+3}$ and so on. The results of the interpolation are, for example, as shown in the solid line in FIG. 12. As a method of interpolation, a value acquired from an arithmetic average (additive average) or geometric average of two direct ray transmittances Cp with respect to adjoining discrete distances (e.g. $L_{s+1}$ and $L_{s+2}$) may be used as direct ray transmittance Cp for the distance between the above adjoining discrete distances. Lagrange interpolation may be used. Or an approximate expression of the solid line in FIG. 12 obtained from the least square method may be used to determine, as direct ray transmittance Cp, a value corresponding to a distance on the solid line. Thus, any commonly used method of interpolation may be employed. The direct ray transmittances Op interpolated by the transmittance interpolating unit 53 are fed to the parameter proofing unit 45 and second intensity estimating unit 54.

(Step S3) Actual Measurement with Phantom

Next, X-ray imaging is carried out in the presence of a subject M. As shown in FIG. 13, acting as the subject M is a phantom Ph in the form of a flat acrylic plate regarded as providing a fixed thickness for direct ray transmission, or the same value of estimated direct ray intensity P for all the pixels. Instead, a water cylinder may be used as phantom Ph.

Returning to the description of this embodiment, X-rays are emitted from the X-ray tube 2 toward the grid 6 and FPD 3 with the acrylic plate phantom Ph interposed between the X-ray tube 2 and grid 6, thereby to carry out X-ray imaging for actual measurement in the presence of the phantom Ph. That is, the X-ray tube 2 emits X-rays in the presence of the phantom Ph, to be incident on the FPD 3 through the grid 6, thereby obtaining actual measurement intensities G with the phantom Ph, which intensities G are intensities after transmission through the grid 6 in actual measurement. Specifically, the detecting elements d of the FPD 3 (see FIG. 3) read the X-rays as converted to electric signals in the presence of phantom Ph, and provide pixel values corresponding to the electric signals.

(Step S4) Estimation and Interpolation of Intensities

The pixel values are equivalent to the actual measurement intensities G after transmission through the grid 6 which are obtained by actual measurement with the phantom Ph. On the other hand, the pixel specifying unit 51 specifies the three adjoining pixels (n−1), n and (n+1) as a combination of three pixels as noted hereinbefore. Based on the direct ray transmittances Cp calculated by the transmittance calculating unit 52, the direct ray transmittances Cp interpolated by the transmittance interpolating unit 53, and the actual measurement intensities G equivalent to the pixel values from the FPD 3, the second intensity estimating unit 54 estimates transmission scattered ray intensities Sc and estimated direct ray intensities P at the three adjoining pixels (n−1), n and (n+1) specified by the pixel specifying unit 51.

The actual measurement intensities G are obtained from the actual measurement in step S3, and are known. The direct ray transmittances Cp are obtained from the actual measurement in step S1 and calculated and interpolated in step S2, and are known. On the other hand, the transmission scattered ray intensities Sc and estimated direct ray intensities P are values to be estimated by the second intensity estimating unit 54, and are unknown at this point of time. Then, the second intensity estimating unit 54 estimates transmission scattered ray intensity Sc and estimated direct ray intensity P by solving simultaneous equations for each of the three adjoining pixels (n−1), n and (n+1).

For the three adjoining pixels (n−1), n and (n+1), the actual measurement intensities G are set to $G_{n-1}$, $G_n$ and $G_{n+1}$, the direct ray transmittances Cp to $Cp_{n-1}$, $Cp_n$ and $Cp_{n+1}$, the transmission scattered ray intensities Sc to $Sc_{n-1}$, $Sc_n$ and $Sc_{n+1}$, and the estimated direct ray intensities P to $P_{n-1}$, $P_n$ and $P_{n+1}$. The transmission scattered ray intensity Sc varies among the three adjoining pixels due to nonuniformity of the grid 6 (scattered radiation removing device), for example. Taking this into consideration, transmission scattered ray intensities Sc at the adjoining pixels are obtained by interpolating calculation. In this embodiment, it is assumed that variations in the transmission scattered ray intensity Sc within the three adjoining pixels (n−1), n and (n+1) can be linearly approximated as in the following the equation (1):

$$Sc_n = (Sc_{n+1} + Sc_{n-1})/2 \tag{1}$$

As a method of interpolating the transmission scattered ray intensities Sc, Lagrange interpolation, for example, may be used as noted in connection with the interpolation of the direct ray transmittances Cp. The method is not limited to equation (1) above, but any commonly used method of interpolation may be employed.

The actual measurement intensities G are expressed by the following simultaneous equations (2)-(4) for the three adjoining pixels (n−1), n and (n+1), showing that each actual measurement intensity G is equal to a sum of the product of estimated direct ray intensity P and direct ray transmittance Cp, and transmission scattered ray intensity Sc:

$$G_{n+1} = P_{n+1} \cdot Cp_{n+1} Sc_{n+1} \tag{2}$$

$$G_n = P_n \cdot Cp_n + Sc_n \tag{3}$$

$$G_{n-1} = P_{n-1} \cdot Cp_{n-1} + Sc_{n-1} \tag{4}$$

Since the acrylic plate used as phantom Ph is formed to have a fixed thickness for direct ray transmission as noted hereinbefore, the estimated direct ray intensities P are equal among the three adjoining pixels as expressed by the following equation (5):

$$P_{n-1} = P_n = P_{n+1} \tag{5}$$

Thus, the pixel specifying unit 51 determines the number of certain pixels to be specified, according to the known number of known direct ray transmittances Cp and the known number of known actual measurement intensities G when estimating the unknown transmission scattered ray intensities Sc and direct ray intensities P at the three adjoining pixels (n−1), n and (n+1) specified by the pixel specifying unit 51. The second intensity estimating unit 54 will estimate the transmission scattered ray intensities Sc and direct ray intensities P by solving the simultaneous equations relating to the actual measurement intensities G, direct ray transmittances Cp, transmission scattered ray intensities Sc and estimated direct ray intensities P for the certain pixels determined, respectively.

In the above, equation (1), the transmission scattered ray intensity Sc at each pixel is obtained by interpolating calculation of transmission scattered ray intensities Sc at the adjoining pixels, and therefore the number of unknowns can be reduced by one. On the other hand, since the above equation (5) shows that the estimated direct ray intensities P are equal among the three adjoining pixels, the number of unknowns is reduced to one. Therefore, apart from the above equations (1) and (5), it is sufficient to form simultaneous equations corresponding to the number of pixels specified. In this case, the simultaneous equations can be solved once the pixel specifying unit 51 specifies only an arbitrary number. In this embodiment, the number is set to three, and simultaneous equations are formed as the above equations (2)-(4).

By solving simultaneous equations obtained from such equations (1)-(5) noted above, the estimated direct ray intensity $P_n(=P_{n+1}=P_{n-1})$, transmission scattered ray intensities $Sc_{n-1}$, $Sc_n$ and $Sc_{n+1}$ are calculated as in the following equations (6)-(9):

$$P_n = (G_{n+1} + G_{n-1} - 2G_n)/(Cp_{n+1} + Cp_{n-1} - 2Cp_n) \tag{6}$$

$$Sc_{n+1} = G_{n+1} P_{n+1} \cdot Cp_{n+1} \tag{7}$$

$$Sc_n = G_n - P_n \cdot Cp_n \tag{8}$$

$$Sc_{n-1} = G_{n-1} - P_{n-1} \cdot Cp_{n-1} \tag{9}$$

In equations (6)-(9) above, the estimated direct ray intensity P is first derived from the above equation (6) using the known actual measurement intensities $G_{n-1}$, $G_n$ and $G_{n+1}$ and known direct ray transmittances $Cp_{n-1}$, $Cp_n$ and $Cp_{n+1}$. After making the estimated direct ray intensity P known, transmission scattered ray intensities $Sc_{n-1}$, $Sc_n$ and $Sc_{n+1}$ are derived from the above equations (7)-(9) using also the estimated direct ray intensity $P_n (=P_{n+1}=P_{n-1})$ now known.

When the combination of three adjoining pixels (n−1), n, and (n+1) is made one group in this way, one estimated direct ray intensity $P_n$ can be found for each group. As described in relation with the above equation (5), the estimated direct ray intensities $P_n$ should essentially have the same value for all the groups, each consisting of three pixels. In practice, however, variations occur under the influence of transmittance variations of scattered rays in peripheral portions of the grid 6, or due to statistical fluctuation errors. In order to reduce the influence of such installation state of the grid 6 or statistical fluctuation errors, an average value of estimated direct ray intensities $P_n$ is obtained from central portions with little experimental errors. When, for example, minor variations occur in the above peripheral portions of the grid 6, the estimated direct ray intensities $P_n$ are obtained, using the above equation (6), for a plurality of groups in central portions of the grid 6, each group consisting of a combination of three pixels (n−1), n and (n+1), and an average value P^ thereof is obtained. The average value P^ is substituted into each of the above equations (2)-(4) (that is, substituted into the following equations (10)-(12) transformed from the above equations (7)-(9)), and the transmission scattered ray intensities $Sc_{n-1}$, $Sc_n$ and $Sc_{n+1}$ are calculated again for all the groups.

$$Sc_{n+1} = G_{n+1} - P^\wedge \cdot Cp_{n+1} \tag{10}$$

$$Sc_n = G_n - P^\wedge \cdot Cp_n \tag{11}$$

$$Sc_{n-1} = G_{n-1} - P^\wedge \cdot Cp_{n-1} \tag{12}$$

Thus, the second intensity estimating unit 54 makes estimations by deriving the transmission scattered ray intensities $Sc_{n-1}$, $Sc_n$ and $Sc_{n+1}$ from the above equations (10)-(12). The transmission scattered ray intensities $Sc_{n-1}$, $Sc_n$ and $Sc_{n+1}$ estimated by the second intensity estimating unit 54 are fed to the intensity interpolating unit 55, rate of change calculating unit 56 and display 5.

Directing attention to the denominator included in the solution of the above simultaneous equations (1)-(5), it is "$Cp_{n+1} + Cp_{n-1} - 2Cp_n$" in this embodiment as seen from the above equation (6). The denominator is "Cp n+1+$Cp_{n-1}$−2$Cp_n$" even when the above equation (6) is substituted into the above equations (7)-(9). When the absolute value of the denominator "$Cp_{n+1}+Cp_{n-1}-2Cp_n$" is a certain value or less, there is a possibility that these simultaneous equations cannot be solved.

Particularly when the denominator "$Cp_{n+1}+Cp_{n-1}-2Cp_n$" is "0", the above simultaneous equations (1)-(5) cannot be solved. When the denominator "$Cp_{n+1}+Cp_{n-1}-2Cp_n$" is "0", that is when the direct ray transmittance $Cp_n$ at the middle pixel of the adjoining pixels is an arithmetical average of direct ray transmittances $Cp_{n+1}$ and $Cp_{n-1}$ of the other pixels ($Cp_{n+1}+Cp_{n-1}-2Cp_n=0$, i.e. $Cp_n=(Cp_{n+1}+Cp_{n-1})/2$), the simultaneous equations cannot be solved if the pixel specifying unit 51 selects the three pixels (n−1), n, and (n+1) as the combination for the simultaneous equations at that time. When the denominator "$Cp_{n+1}+Cp_{n-1}-2Cp_n$" is "0", the pixel specifying unit 51, preferably, does not select the three pixels (n−1), n and (n+1) as the combination for the simultaneous equations, but selects three different pixels (n'−1), n' and (n'+1) (e.g. pixels n, (n+1) and (n+2), or pixels (n−2), (n−1) and n) as the combination. Then, the above simultaneous equations (1)-(5) of the three different pixels (n'−1), n' and (n'+1) specified are solved.

With the pixels specified as described above, the simultaneous equations can be solved, and using the estimated direct ray intensities $P_n$, an average value of the estimated direct ray intensities $P_n$ is obtained by the above method. Once average value P^ of the estimated direct ray intensities $P_n$ is obtained, transmission scattered ray intensities $Sc_{n-1}$, $Sc_n$ and $Sc_{n+1}$ of the three pixels (n−1), n and (n+1) forming the combination when the denominator "$Cp_{n+1}+Cp_{n-1}-2Cp_n$" is "0" can also be derived from the above equations (10)-(12).

To summarize the description about solving the simultaneous equations, the estimated direct ray intensities $P_n(=P_{n+1}=P_{n-1})$ when the denominator "$Cp_{n+1}+Cp_{n-1}-2Cp_n$" is not "0" are derived from the above equation (6), and average value P^ is obtained. The average value P^ is substituted into the above equations (10)-(12) to obtain the transmission scattered ray intensities $Sc_{n-1}$, $Sc_n$ and $Sc_{n+1}$ when the denominator "$Cp_{n+1}+Cp_{n-1}-2Cp_n$" is not "0". The transmission scattered ray intensities $Sc_{n-1}$, $Sc_n$, and $Sc_{n+1}$ when the denominator "$Cp_{n+1}+Cp_{n-1}-2Cp_n$" is "0" can also be obtained by similar substitution into the above equations (10)-(12). In this way, the estimated direct ray intensities P when the denominator "$Cp_{n+1}+Cp_{n-1}-2Cp_n$" is "0" are first obtained to obtain average value P^. Then, the average value P^ is used to obtain the transmission scattered ray intensities $Sc_{n-1}$, $Sc_n$ and $Sc_{n+1}$ when the denominator "$Cp_{n+1}+Cp_{n-1}-2Cp_n$" is not "0", and the transmission scattered ray intensities $Sc_{n-1}$, $Sc_n$ and $Sc_{n+1}$ when the denominator "$Cp_{n+1}+Cp_{n-1}-2Cp_n$" is "0" are obtained similarly.

In this method, the subject is the phantom Ph in the form of an acrylic plate, and variations in the estimated direct ray intensity P are known and smooth. These facts are used to obtain the estimated direct ray intensity P (average value P^ in this embodiment) by smoothing and interpolating calculations of the estimated direct ray intensities P obtained about the pixels (specified pixels) first determined by the pixel specifying unit 51, or by calculating an average value of the estimated direct ray intensities P. The estimated direct ray intensity P obtained has a value close to a true value since variations of the estimated direct ray intensity P are smooth, and averaging or smoothing is effective in reducing variations due to statistical fluctuation errors. The transmission scattered ray intensities Sc are obtained directly by substituting the estimated direct ray intensity P close to the true value into the above equations (2)-(4). This provides a great advantage of causing no deterioration in the resolution of images of the transmission scattered ray intensities Sc since averaging or smoothing and interpolating calculations are not carried out. The resolution of the transmission scattered ray intensities Sc is maintained, and minute variations in the transmission scattered ray intensity Sc due to deformation of the grid foil strips can be determined accurately.

As another method, for example, transmission scattered ray intensities $Sc_{n-1}$, $Sc_n$ and $Sc_{n+1}$ when the denominator "$Cp_{n+1}+Cp_{n-1}-2Cp_n$" is not "0" may be obtained before the estimated direct ray intensities P. By interpolating the transmission scattered ray intensities $Sc_{n-1}$, $Sc_n$ and $Sc_{n+1}$, transmission scattered ray intensities $Sc_{n-1}$, $Sc_n$ and $Sc_{n+1}$ when the denominator "$Cp_{n+1}+Cp_{n-1}-2Cp_n$" is "0" are obtained. By substituting the obtained transmission scattered ray intensities $Sc_{n-1}$, $Sc_n$ and $Sc_{n+1}$ into the above equations (7)-(9), estimated direct ray intensities P when the denominator "$Cp_{n+1}+Cp_{n-1}-2Cp_n$" is not "0" and when the denominator "$Cp_{n+1}+Cp_{n-1}-2Cp_n$" is "0" are obtained. An average value P^ of a plurality of estimated direct ray intensities $P_n$ of the combination of three pixels (n−1), n and (n+1) in the central portion of the grid 6, including when the denominator "$Cp_{n+1}+Cp_{n-1}-2Cp_n$" is "0", is obtained. By substituting this average value P^ into the above equations (10)-(12), transmission scattered ray intensities $Sc_{n-1}$, $Sc_n$ and $Sc_{n+1}$ may be obtained again. The transmission scattered ray intensities $Sc_{n-1}$, $Sc_n$ and $Sc_{n+1}$ obtained again may be used to obtain rates of change Rcs in step S5 described hereinafter.

(Step S5) Calculation and Interpolation of Rates of Change

The rate of change calculating unit 56 calculates rates of change Rcs using the transmission scattered ray intensities Sc ($Sc_{n-1}$, $Sc_n$ and $Sc_{n+1}$) estimated by the second intensity estimating unit 54. Specifically, an average value Sc^ is obtained, or values Sc~ of pixels are obtained by smoothing and interpolating calculations, in order to determine the rates of change Rcs of the pixels relative to the values of all the pixels as reference intensities of the transmission scattered ray intensities Sc. Assuming that a ratio between the transmission scattered ray intensity $Sc_n$ of each pixel and the average value Sc^ or the value Sc~ of each pixel is a rate of change Rcs, and that $Rcs_n$ represents the rate of change Rcs of each pixel, $Rcs_n$ is expressed by the following equation (13):

$$Rcs_n = Sc_n/Sc\hat{\ }$$

$$\text{or } Rcs_n = Sc_n/Sc\sim \quad (13)$$

A reference estimated scattering intensity used as the denominator when calculating the rates of change of transmission scattered rays corresponds to scattered ray intensity in the case of an ideal grid with no distortion of the foil strips or not dependent on installation conditions.

As a method therefor may use:
1) an average value by simply approximating a scattered ray intensity distribution two-dimensionally fixed; or
2) a value acquired by two-dimensionally smoothing and interpolating the estimated scattered ray intensity of each pixel, by strictly taking into consideration scattered ray intensity variations due to installation conditions, such as the shape of the phantom and peripheral portions of the grid. The average value of 1) can be said the simplest method of smoothing and interpolating calculations.

Thus, variations of transmission scattered ray intensity Sc, for which installation conditions of the grid 6 relating to deformation of the absorbing foil strips 6a, for example, are considered by using the ratio relative to the reference value, are expressed by the rates of change $Rcs_n$. The rate of change calculating unit 56 calculates the rates of change $Rcs_n$ for all the pixels. The rate of change interpolating unit 57 interpolates, as necessary, the rates of change $Rcs_{n-1}$, $Rcs_n$ and $Rcs_{n+1}$ calculated by the rate of change calculating unit 56, and then feeds the rates of change to the second intensity estimating unit 54 again. The rates of change $Rcs_{n-1}$, $Rcs_n$ and $Rcs_{n+1}$ calculated by the rate of change calculating unit 56 or interpolated by the rate of change interpolating unit 57 are fed also to the parameter proofing unit 45.

The rate of change Rcs, as does the direct ray transmittance Cp, varies for each of the discrete distances $L_{s+1}$, $L_{s+2}$, $L_{s+3}$ and so on as shown in black squares in FIG. 11. The rate of change interpolating unit 57 interpolates the rates of change Rcs calculated by the rate of change calculating unit 56 in distances around the discrete distances $L_{s+1}$, $L_{s+2}$, $L_{s+3}$ and so on. The results of the interpolation are, for example, as shown in the dotted line in FIG. 12. As a method of interpolation, a value acquired from an arithmetic average (additive average) or geometric average of two rates of change Rcs with respect to adjoining discrete distances (e.g. $L_{s+1}$ and $L_{s+2}$) may be used as rate of change Rcs for the distance between the above adjoining discrete distances. Lagrange interpolation may be used. Or an approximate expression of the dotted line in FIG. 12 obtained from the least square method may be used to determine, as rate of change Rcs, a value corresponding to a distance on the dotted line. Thus, any commonly used method of interpolation may be employed.

As described above, for the direct ray transmittances Cp, and also for the rates of change Rcs, interpolation is carried out taking the discrete distances $L_{s+1}$, $L_{s+2}$, $L_{s+3}$ and so on into consideration. These distances L ($=L_{s+1}$, $L_{s+2}$, $L_{s+3}$ and so on) are distances SID of the X-ray tube 2 to the FPD 3 in the direction of perpendicular PL from the X-ray tube 2 to the FPD 3 as noted hereinbefore. Even if the direct ray transmittances Cp and the rates of change Rcs are interpolated in relation to the SID, a shift from the direction of arrangement of the absorbing foil strips 6a will necessitate interpolation even for the same SID. Thus, in order to grasp also the direction of arrangement of the absorbing foil strips 6a for interpolating the direct ray transmittances Cp and the rates of change Rcs, at the time of X-ray imaging using a subject M other than the phantom Ph, the first intensity estimating unit 41 estimates intensities on an assumption that shadows do not fall as in step S7 to be described hereinafter, the shadow position calculating unit 42 calculates shadow positions as in step S8, and the focal position calculating unit 43 calculates a focal position as in step S9. In this specification, the interpolation taking also the direction of arrangement of the absorbing foil strips 6a into consideration is defined as "proofing", which will be described hereinafter as distinguished from the interpolation taking only the distances SID into consideration.

In order to obtain, in step S8, shadow positions in the presence of a real subject M instead of the phantom Ph, actual measurement is carried out for a relationship between X-ray intensity and reference position as in the flow of FIG. 10 before actual measurement (that is, actual X-ray imaging) in the presence of the real subject as in step S6 to be described hereinafter. This flow of FIG. 10 may be executed at any time before step S6, and thus, for example, may be executed before step S1 in FIG. 9, or after step S5 in FIG. 9, or may be executed in parallel with steps S1-S5 in FIG. 9. Through this actual measurement, a relationship (graph) between shadow position and X-ray intensity shown in FIG. 14 is acquired.

The relationship between the X-ray intensities of the pixel columns (c, d and e in FIG. 6) with the shadows 33 falling on at least part thereof in the absence of a subject, and shadow positions matched therewith, is not limited to the relationship (graph) shown in FIG. 14. In order to create such relationship, it is not absolutely necessary to execute the flow (actual measurement) of FIG. 10. For example, such relationship may be a relationship between a plurality of shadow positions in the absence of a subject, and a ratio between an area of a shadowed portion in each shadow position and a total area of the pixel with the shadow falling on at least part thereof.

This relationship uses the fact that the X-ray intensity of the pixels (in this case, pixel columns c, d and e) with the shadows 33 falling on at least part thereof is proportional to the ratio between an area of a shadowed portion in each shadow position and a total area of the pixel with the shadow 33 falling on at least part thereof. That is, when the shadow positions are moved virtually, a ratio between an area of a portion with the shadow 33 and a total area of the pixel, among the pixels under the shadows 33, can be determined without actual measurement. Therefore, by obtaining this ratio each time the shadow positions are virtually moved, a relationship between the shadow position and the ratio matched therewith can be obtained without actual measurement. X-ray intensity can be regarded as proportional to this ratio. That is, if the ratio is small, the portions of the pixels with the shadows 33 are large and X-ray intensity is also small. Conversely, if the ratio is large, the portions of the pixels with the shadows are small and X-ray intensity is also large. By using the proportionality of X-ray intensity to the ratio as above, the relationship between the X-ray intensities of the pixels with the shadows 33 falling on at least part thereof in the absence of a subject, and shadow positions matched therewith, can be obtained without actual measurement. In order to create the relationship shown in FIG. 14, the flow (actual measurement) in FIG. 10 is executed in this embodiment as described hereinafter.

(Step T1) Movement of Grid

The entire grid 6 is moved, in the absence of a subject, in order to move the marking absorbers 7 stepwise along the direction of arrangement (Y-direction) of the absorbing foil strips 6a. Here, the entire grid 6 is moved in B⁻ direction parallel to the Y-direction in FIG. 4 (c). The X-ray tube 2 and FPD 3 are maintained still. Focusing attention on the pixel column c, the entire grid 6 is moved in B⁻ direction, starting at a position where the shadows 33 do not yet fall on the pixel column c. The entire grid 6 is moved in B⁻ direction, with the shadows 33 beginning to fall on the pixel column c, and as far as a position where the pixel column c completely comes under (i.e. is covered by) the shadows 33. During this movement of the grid 6, the marking absorbers 7 will pass through the reference position with the perpendicular PL extending from the focus F of the X-ray tube 2 to the FPD 3. In FIG. 13, when the reference position is set to "0", the grid 6 is moved at intervals of 0.0125 mm (=12.5 µm) from a position −74 µm from the reference position to a position +150 µm from the reference position. In moving the grid 6 along the Y-direction, when moving it by minute distances, the movement may be made by using the Y-direction adjust screws 60y of the moving mechanism 60 described hereinbefore and shown in FIG. 7. For distances longer than the moving distances (minute distances) by the Y-direction adjust screws 60y, the movement may be made by using a moving device other than the moving mechanism 60.

(Step T2) Actual Measurement without Subject

The grid 6 is moved every predetermined pitch (0.0125 mm here) in step T1, and in positions of the movement, X-ray imaging is carried out in the absence of a subject. As in step S1, the X-ray tube 2 emits X-rays in the absence of a subject, to be incident on the FPD 3 through the grid 6, thereby obtaining actual measurement data without a subject. Specifically, the detecting elements c of the FPD 3 (see FIG. 3) convert the X-rays in the absence of a subject, into electric signals for read-out, and converts the electric signals into pixel value corresponding thereto.

The pixel values are equivalent to intensity I after transmission through the grid 6 obtained by actual measurement in the absence of a subject. In this embodiment, the FPD 3 detects X-ray intensities of the pixel columns b, c and d, and obtains average intensities Ib, Ic and Id of the X-ray intensities longitudinally of the pixel columns b, c and d by actual measurement. The shadow positions and average intensities Ib, Ic and Id at that time are plotted in a corresponding relationship.

(Step T3) Moved to Position where all is Under Shadows?

When, in step T1, the entire grid 6 has moved to a position where the pixel column c completely comes under the shadows 33, the series of steps in FIG. 10 is ended noting that the relationship (graph) shown in FIG. 14 is completed. When, in step T1, the entire grid 6 has not moved to the position where the pixel column c completely comes under the shadows 33, it is noted that the relationship (graph) shown in FIG. 14 is not completed. Then, the operation returns to step T1 and repeats steps T1-T3.

By repeating the above steps T1-T3, the shadow positions and average intensities Ib, Ic and Id matched therewith are plotted, respectively, to create the relationship shown in FIG. 14. Assuming the X-ray intensity (average intensity here) $Ic^0$ at the time the shadows 33 do not fall on the pixel column c, as shown in FIG. 14, the X-ray intensity Ic is $Ic^0$ at the time of the starting point which is a position before the shadows 33 fall on the pixel column c. As the shadows 33 begin to fall on the pixel column c, X-ray intensity Ic will decrease gradually. When the shadows 33 fall on the entire pixel column c, X-ray intensity Ic will become "0". FIG. 6 shows a state at the time of the reference position, in which the shadows 33 fall on part of the pixel column c. It is shown also in FIG. 14 that, when the shadow position is the reference position, X-ray intensity Ic is smaller than $Ic^0$ and larger than "0".

(Step S6) Actual Measurement with Real Subject

Next, X-ray imaging is carried out in the presence of a subject M other than the subject M (phantom Ph) used in steps S3-S5. As shown in FIG. 1, a real subject M is used for actual X-ray imaging. X-rays are emitted from the X-ray tube 2 toward the grid 6 and FPD 3 with the real subject M interposed between the X-ray tube 2 and grid 6, thereby to carry out X-ray imaging for actual measurement with the real subject M. That is, the X-ray tube 2 emits X-rays in the presence of the real subject M (i.e. subject M for use in actual X-ray imaging), to be incident on the FPD 3 through the grid 6. In this way, actual measurement intensities G which are intensities after transmission through the grid 6 in the actual measurement in the presence of the subject M are obtained as in step S3. Specifically, the detecting elements d of the FPD 3 (see FIG. 3) read the X-rays as converted to electric signals in the presence of the subject M, and provide pixel values corresponding to the electric signals.

At this time, the X-ray intensities of the shadow pixels 34 shown in FIG. 6 are also detected, to acquire also actual measurement intensities of the shadow pixels 34. As noted hereinbefore, the average intensities of the X-ray intensities longitudinally of the pixel columns a, b, f and g free of the shadows 33 are set to $Ia^0$, $Ib^0$, $If^0$ and $Ig^0$, respectively, and the average intensities of the X-ray intensities longitudinally of the pixel columns c, d and e which are at least partly under the shadows 33 are set to Ic, Id and Ie, respectively.

(Step S7) Estimation of Intensities on Assumption of being Free of Shadows

The first intensity estimating unit 41 estimates X-ray intensities $Ic^{0'}$, $Id^{0'}$ and $Ie^{0'}$, by interpolating the X-ray intensities (average intensities) Ic, Id and Ie of the pixel columns c, d, and e with the shadows 33 falling on at least part thereof, which are obtained in step S6, based on the X-ray intensities (average intensities here) $Ia^0$, $Ib^0$, $If^0$ and $Ig^0$ of the pixel columns a, b, f and g also obtained in step S6. That is, X-ray intensities $Ic^{0'}$, $Id^{0'}$ and $Ie^{0'}$ in the presence of the subject M are estimated on an assumption that that the pixel columns c, d and e are free of the shadows 33.

For this purpose, as shown in black dots in FIG. 15, the X-ray intensities $Ia^0$, $Ib^0$, $If^0$ and $Ig^0$ of the pixel columns a, b, f and g obtained in step S6, and the pixel columns a, b, f, and g, are plotted as matched with each other, and the X-ray intensities Ic, Id and Ie of the pixel columns c, d, and e obtained in step S6, and the pixel columns c, d and e, are plotted as matched with each other. Although the shadow positions shift slightly because the focal position moves in the presence of the subject M, FIG. 15 shows that the pixel columns c, d and e with the shadows 33 falling thereon have the intensities Ic, Id and Ie which are far lower than the intensities $Ia^0$, $Ib^0$, $If^0$ and $Ig^0$ of the other pixel columns. In this embodiment, the X-ray intensities $Ic^{0'}$, $Id^{0'}$ and $Ie^{0'}$ are estimated by smoothing and interpolating calculations of the X-ray intensities $Ia^0$, $Ib^0$, $If^0$ and $Ig^0$, as are the direct ray transmittances Cp and rates of change Rcs. The X-ray intensities $Ic^{0'}$, $Id^{0'}$ and $Ie^{0'}$ estimated by the first intensity estimating unit 41 are fed to the shadow position calculating unit 42.

(Step S8) Calculation of Shadow Positions

The shadow position calculating unit 42 calculates shadow positions in the presence of the subject M, based on the X-ray intensity Ic (i.e. the actual measurement intensity Ic) of the pixel column c obtained in step S6, the intensities $Ic^{0'}$, $Id^{0'}$ and $Ie^{0'}$ estimated by the first intensity estimating unit 41, and the relationship (see FIG. 14) between the X-ray intensities of the pixel columns c, d and e with the shadows 33 falling on at least part thereof and the shadow positions, which is obtained in steps T1-T3 in the absence of a subject M.

When the graph of the relationship as shown in FIG. 14 is used, $Ic/Ic^0$ which is a ratio between the X-ray intensity Ic of the pixel column c with the shadows 33 falling on at least part thereof, which is obtained by the actual measurement in step T2 in the absence of a subject, and the X-ray intensity $Ic^0$ when the shadows 33 do not fall on the pixel column c, can be obtained from FIG. 14. In other words, when the graph in FIG. 14 is normalized by $Ic^0$ (divided by $Ic^0$), this will result in a graph of a plurality of shadow positions provided by moving, in the absence of a subject M, the marking absorbers 7 stepwise along the direction of arrangement (B⁻ direction in FIG. 6 (c)) of the absorbing foil strips 6a, and the ratio Ic/Ic between the X-ray intensity Ic of the pixel column c with the shadows 33 falling on at least part thereof in each shadow position and the X-ray intensity $Ic^0$ when the shadows 33 do not fall on the pixel column c. On the other hand, $Ic/Ic^{0'}$, which is a ratio between the X-ray intensity Ic (i.e. the actual measurement intensity Ic) of the pixel column c obtained in step S6 and the intensity $Ic^{0'}$ estimated by the first intensity estimating unit 41, is obtained.

The ratio $Ic/Ic^0$ in the absence of a subject is obtained from the graph in FIG. 14. The ratio $Ic/Ic^{0'}$ in the presence of a subject M is assumed equal to the ratio $Ic/Ic^0$ in the absence of a subject. Shadow positions xg with the ratio $Ic/Ic^0$ (in the absence of a subject), which is equal to the ratio $Ic/Ic^{0'}$ between the actual measurement intensity Ic of the pixel column c obtained in step S6 and the intensity $Ic^{0'}$ estimated by the first intensity estimating unit 41, are obtained from FIG. 14. By using the fact that the actual measurement intensity Ic of the pixel column c with the shadows 33 falling on at least part thereof is proportional to the ratio $Ic/Ic^0$ between the X-ray intensity Ic of the pixel column c with the shadows 33 falling at least part thereof in each shadow position and the X-ray intensity $Ic^0$ when the shadows 33 do not fall on the pixel column c, the relationship between the X-ray intensity of the pixel column c with the shadows 33 falling on at least part thereof in the absence of a subject and the shadow positions matched therewith can be obtained from the actual measurement in which the marking absorbers 7 are moved stepwise along the direction of arrangement of the absorbing foil strips 6a. This embodiment has been described as obtaining the shadow positions xg from the intensity Ic of the pixel column c since the graph in FIG. 14 is a graph focusing attention on the pixel column c. Besides the pixel column c, the shadow positions xg can be obtained, as from the intensity Ic, also from intensities Id and Ie of the pixel columns d and e, with the shadows 33 falling thereon.

Thus, the shadow position calculating unit 42 obtains the shadow positions xg in the presence of the subject M, based on (A) the X-ray intensity Ic of the pixel column c with the shadows falling on at least part thereof provided by the actual measurement by the FPD 3 in the presence of the subject M, (B) the X-ray intensities $Ic^{0'}$, $Id^{0'}$ and $Ie^{0'}$ estimated by the first intensity estimating unit 41, and (C) the relationship between the X-ray intensity of the pixel column c with the shadows 33 falling on at least part thereof in the absence of a subject and the shadow positions matched therewith (see FIG. 14). The shadow positions xg in the presence of the subject M obtained by the shadow position calculating unit 42 are fed to the focal position calculating unit 43.

(Step S9) Calculation of Focal Position

The focal position calculating unit 43 calculates the focal position Xf of the FPD 3 relative to the X-ray tube 2 in the presence of the subject M, based on the shadow positions xg (which are $x_0^{L'}$ and $x_0^{R'}$ here to be described hereinafter) in the presence of the subject M calculated by the shadow position calculating unit 42, the distance d between the absorbing foil strips 6 and FPD 3, and the shadow positions xg (which are here $x_0^L$ and $x_0^R$ to be described hereinafter) relative to the reference position with the perpendicular PL extending from the focus F of the X-ray tube 2 to the FPD 3 in the absence of a subject.

As shown in FIG. 16, the distance from the center of the grid 6 the left end of the upper left absorber 71 is represented by $Wg^L$, and the distance from the center of the grid 6 to the right end of the lower right absorber 72 is represented by $Wg^R$. The coordinate of the reference position with the perpendicular PL extending from the focus F of the X-ray tube 2 to the FPD 3 at the reference SID ($L_0$) in the absence of a subject is represented by $X_0=0$, the shadow position of the upper left absorber 71 from the reference position $X_0$ is represented by $x_0^L$, and the shadow position of the lower right absorber 72 from the reference position $X_0$ is represented by $x_0^R$. The SID in the presence of the subject M is represented by L. At the SID (L), the shadow position of the upper left absorber 71 from the reference position $X_0$ is represented by $x_0^{L'}$, and the shadow position of the lower right absorber 72 from the reference position $X_0$ is represented by $x_0^{R'}$.

Even if the focal position moves longitudinally of t absorbing foil strips 6a (X-direction which is a direction normal to the plane of FIG. 16), the movement will cause variations in the proofing parameters at only a negligible practical level. Thus, a moving distance between axes, from a radiation axis between $L_0$ and $X_0$ on the perpendicular PL in the absence of a subject to a radiation axis in the presence of the subject M is regarded as the focal position Xf. Focusing attention on the shadow 33 of the left end of the upper left absorber 71, it is expressed by the following equations (14) and (15) based on simple geometric calculations:

$$x_0^L = L \cdot Wg^L/(L-d-h) \qquad (14)$$

$$Xf = (x_0^{L'} - x_0^L) \cdot (L-d-h)/(d+h) \qquad (15)$$

The distance $Wg^L$ from the center of the grid 6 to the left end of the upper left absorber 71, the distance d between the absorbing foil strips 6a and the FPD 3, and the height h of the absorbing foil strips 6a, are known. When the SID (L) in the presence of the subject M at the time of X-ray imaging is also known from hardware information on the apparatus or the like, the shadow position $x_0^L$ of the upper left absorber 71 in the absence of a subject is derived from the above equation (14). The shadow position $x_0^{L'}$ of the upper left absorber 71 in the absence of a subject obtained as above, and the shadow position $x_0^{L'}$ of the upper left absorber 71 in the presence of the subject M calculated by the shadow position calculating unit 42 in step S8, are substituted into the above equation (15), thereby to obtain the focal position Xf of the FPD 3 relative to the X-ray tube 2 in the presence of the subject M.

On the other hand, when the SID (L) in the presence of the subject M at the time of X-ray imaging is unknown, the focal position Xf is derived, after L is derived, from the following equations (16) and (17) similar to the above equations (14) and (15):

$$x_0^R = L \cdot Wg^R/(L-d) \qquad (16)$$

$$Xf = (x_0^{R'} - x_0^R) \cdot (L-d-h)/(d+h) \qquad (17)$$

By erasing $x_0^L$ and $x_0^R$ from the above equations (14)-(17), the following equation (18) is obtained.

$$L = (x_0^{L'} - x_0^{R'}) \cdot d \cdot (d+h) / \{(x_0^{L'} - Wg^L) \cdot d - (x_0^{R'} - Wg^R) \cdot (d+h)\} \qquad (18)$$

The distance $Wg^R$ from the center of the grid 6 to the right end of the lower right absorber 72 is known. By substituting the known distance $Wg^R$ into the above equation (18), and substituting the shadow position $x_0^{R'}$ of the lower right absorber 72 in the presence of the subject M calculated by the shadow position calculating unit 42 in step S8, SID (L) in the presence of the subject M is calculated. That is, since the shadow positions xg ($x_0^{L'}$ and $x_0^{R'}$) in the presence of the subject M are calculated in step S8, SID (L) in the presence of the subject M is calculated by substituting into the above equation (18) the shadow positions xg calculated, and the distances $Wg^L$ and $Wg^R$, the distance d between the absorbing foil strips 6a and the FPD 3 and the height h of the absorbing foil strips 6a which are known. The focal position Xf can be obtained by substituting the calculated SID (L) into the above equations (14) and (15) or the above equations (16) and (17).

Thus, based on (a) the shadow positions xg ($x_0^{L'}$ and $x_0^{R'}$) in the presence of the subject M calculated by the shadow position calculating unit 42, (b) the distance d between the absorbing foil strips 6a and the FPD 3, and (c) the shadow positions xg ($x_0^L$ and $x_0^R$) relative to the reference position $X_0$ with the perpendicular PL extending from the focus F of the X-ray tube 2 to the FPD 3 in the absence of the subject M, the focal position calculating unit 43 calculates the focal position Xf of the FPD 3 relative to the X-ray tube 2 in the presence of the subject M. The focal position Xf in the presence of the subject M calculated by the focal position calculating unit 43 is fed to the parameter proofing unit 45.

(Step S10) Proofing of Parameters

The direct ray transmittances Cp and the rates of change Rcs are proofed based on the relationship between the direct ray transmittances Cp and the rates of change Rcs (relating to the transmission scattered ray intensities Sc), which are the physical quantities calculated before X-ray imaging, and the focal position Xf of the X-ray tube 2 relative to the FPD 3 matched therewith, and the focal position Xf in the presence of the subject M calculated by the focal position calculating unit 43.

As described hereinbefore, the direct ray transmittances Cp and also the rates of change Rcs are interpolated by the transmittance interpolating unit 53 and the rate of change interpolating unit 57 taking the discrete distances $L_{s+1}$, $L_{s+2}$, $L_{s+3}$ and so on into consideration, but the direction of arrangement of the absorbing foil strips 6a is not taken into consideration. Thus, the parameters (direct ray transmittances Cp and rates of change Rcs) are proofed in step S10 in order to carry out interpolation (proofing) considering also the direction of arrangement of the absorbing foil strips 6a. In this proofing, since discrete values $(L_1, L_2, \ldots, L_m, L_{m+1}, \ldots)$ of SID (L) are also considered, it is not absolutely necessary for the transmittance interpolating unit 53 or the rate of change interpolating unit 57 to carry out interpolation considering the discrete distances. Only the direct ray transmittances Cp calculated by the transmittance calculating unit 52 and the rates of change Rcs calculated by the rate of change calculating unit 56 may be fed to the parameter proofing unit 45.

Specifically, as shown in FIG. 17, direct ray transmittance Cp and rate of change Rcs are obtained before X-ray imaging for each of the discrete SIDs $(L_1, L_2, \ldots, L_m, L_{m+1}, \ldots)$ and each of the discrete focal positions $(Xf_{-n}, Xf_{-n+1}, Xf_{-n+2}, \ldots, Xf_0, \ldots, Xf_{n-2}, Xf_{n-1}$ and $Xf_n)$ in the direction of arrangement (Y-direction) of the absorbing foil strips 6a. As for the method of calculating the direct ray transmittances Cp and rates of change Rcs, steps S1-S9 may be executed to obtain them beforehand essentially while moving the X-ray tube 2 discretely as shown in FIG. 17, using the phantom Ph or the same subject M used in the actual X-ray imaging. In this way, the relationship between the parameters (direct ray transmittances Cp and the rates of change Rcs) and the focal positions Xf of the X-ray tube 2 relative to the FPD 3 matched therewith is obtained before the X-ray imaging.

In practice, however, when the X-ray tube 2 is moved, the radiation emitting device represented by the X-ray tube 2 is heavy as noted hereinbefore, and when such heavy X-ray tube 2 is moved parallel to the direction of arrangement (Y-direction) of the foil strips 6a (of the grid 6), there will occur a problem that, even if moving distances are set finely, actual moving distances become different from the set moving distances. This problem occurs not only with the X-ray tube 2, but also with the radiation detecting device represented by the FPD 3 interlocked to the movement of the X-ray tube 2. Then, a change has been made in the concept of carrying out radiation imaging (X-ray imaging in this embodiment) by moving the radiation emitting device represented by the X-ray tube 2 or the radiation detecting device represented by the FPD 3, or using the data obtained by moving the radiation emitting device (X-ray tube 2 in this embodiment) or the radiation detecting device (FPD 3 in this embodiment) in the radiation imaging (X-ray imaging in this embodiment). Consequently, it has been contrived to move the scattered radiation removing device (grid 6 in this embodiment) which is lighter than the radiation emission device (X-ray tube 2 in this embodiment) and the radiation detecting device (FPD 3 in this embodiment).

That is, the Y-direction adjust screws 60y of the moving mechanism 60 (see FIG. 7) move the grid 6 parallel to the direction of arrangement (Y-direction) of the absorbing layers 6a. Assume, for example, that the X-ray tube 2 is to be moved from a state as shown in FIG. 18 (a), in a B⁻ direction of the Y-direction as shown in FIG. 18 (b). Focusing attention on the g-th absorbing foil strip 6a, it is assumed that the shadow 32 (see also FIGS. 4 and 6) of this absorbing foil strip 6a straddles a plurality of pixels centering on the k-th pixel from the reference position $X_0$ (see FIG. 16) with the perpendicular PL extending from the focus F of the X-ray tube 2 to the FPD 3. In this embodiment, it is assumed that, as shown in FIG. 18 (a), the shadow 32 of the g-th absorbing foil strip 6a on which attention is focused straddles three pixels (k−1), k and (k+1). It should be noted that, although the width of the absorbing foil strip 6a shown thick in FIG. 18 for the convenience in showing the shadow 32 as enlarged, the actual width of the absorbing foil strip 6a is thin.

When the X-ray tube 2 is to be moved from the state shown in FIG. 18 (a), in the B⁻ direction of the Y-direction as shown in FIG. 18 (b), the X-ray tube 2 is moved virtually by an integral multiple (e.g. m=2 when the integer is m) of the interval between the pixels (i.e. pixel pitch Wd). When the pixel pitch Wd=0.15 mm and m=2 as above, the X-ray tube 2 moves virtually at intervals of 0.3 mm (=0.15 mm×2=Wd×m) from the reference position $X_0$=0. Only if the parameters (direct ray transmittances Cp and rates of change Rcs) at the three pixels (k−1), k and (k+1) when the X-ray tube 2 moves virtually are finally obtained, parameters when the X-ray tube 2 has moved Wd×m can be obtained among the relationships between the parameters and the focal positions of the X-ray tube 2 relative to the FPD 3 matched therewith, shown in FIG. 17.

For this purpose, instead of actually moving the X-ray tube 2, the Y-direction adjust screws 60y of the moving mechanism 60 (see FIG. 7) move the grid 6 from the state shown in FIG. 18 (a), in a B⁺ direction of the Y-direction direction as shown in FIG. 18 (c). The B⁺ direction is a direction opposite to the B⁻ direction noted above. On the basis of the B⁺ direction, it can be considered that the X-ray tube 2 is moved virtually by an integral multiple (e.g. m=2) of the interval between the pixels (i.e. pixel pitch Wd) in the B⁻ direction opposite to the B⁺ direction which is the direction of movement by the Y-direction adjust screws 60y of the moving mechanism 60. With this movement of the grid 6 in the B⁺ direction, the g-th absorbing foil strip 6a also moves Wd×m. The absorbing foil strip 6a after this movement is regarded as the $g_m$-th in order. As shown in FIG. 18 (c), the shadow 32 of this $g_m$-th absorbing foil strip 6a falls on the pixels (k−m−1), (k−m) and (k−m+1) which have moved Wd×m from the three pixels (k−1), k and (k+1), respectively.

A figure (right triangle), shown in FIG. 18 (b), which is defined by the perpendicular L extending from the focus F of the X-ray tube 2 to the FPD 3, the detecting plane of the FPD 3 and irradiated radiation extending from the shadow 32 of the g-th absorbing foil strip 6a (or the pixels (k−1), k d (k+1)) to the focus F of the X-ray tube 2, and a figure (right triangle), shown in FIG. 18 (c), which is defined by the perpendicular L extending from the focus F of the X-ray tube 2 to the FPD 3, the detecting plane of the FPD 3 and irradiated radiation extending from the shadow 32 of the gm-th absorbing foil strip 6a (or the pixels (k−m−1), (k−m) and (k−m+1)) to the focus F of the X-ray tube 2, are congruent. Therefore, the calculation of the direct ray transmittances Cp and rates of change Rcs at the three pixels (k−1), k and (k+1) which should be obtained virtually is replaceable by the calculation of the direct ray transmittances Cp and rates of change Rcs at the three pixels (k−m−1), (k−m) and (k−m+1) by the transmittance calculating unit 52, transmittance interpolating unit 53, rate of change calculating unit 56 and rate of change interpolating unit 57, with X-rays emitted from the X-ray tube 2 after the grid 6 has been moved Wd×m by the Y-direction adjust screws 60y of the moving mechanism 60. That is, the correcting unit 44 can correct the direct ray transmittances Cp and rates of change Rcs at the three pixels (k−1), k and (k+1) which should be obtained virtually, as the direct ray transmittances Cp and rates of change Rcs at the three pixels (k−m−1), (k−m) and (k−m+1) obtained by emitting X-rays from the X-ray unit after the grid 6 has been moved Wd×m by the Y-direction adjust screws 60y of the moving mechanism 60.

For the other absorbing foil strips 6a not shown in FIG. 16, the positional relationship between the absorbing foil strips 6a of the grid 6 and the shadow positions is also the same. The values of the direct ray transmittances Cp and rates of change Rcs at the respective pixels obtained by virtually moving the X-ray tube 2 Wd×m in the B⁻ direction opposite to the B⁺ direction which is the direction of movement by the Y-direction adjust screws 60y are replaceable by the values of the direct ray transmittances Cp and rates of change Rcs obtained by moving the X-ray tube 2 Wd×m in the B⁺ direction with the Y-direction adjust screws 60y. It is also the same when the grid 6 is moved in the B⁻ direction by the Y-direction adjustment screws 60y.

While the actual movement of the grid 6 has been described taking the shadows 32 of the absorbing foil strips 6a for example, correction can be made by using the direct ray transmittances Cp and rates of change Rcs at the pixels under the shadows 33 of the marking absorbers 7 used in this embodiment. In this embodiment, since the shadows 33 of the marking absorbers 7 straddle three pixels as shown in FIG. 6, it is applicable to the shadows 33 of the marking absorbers 7. When calculating (including also interpolating) direct ray transmittances Cp, the direct ray transmittance Cp can be acquired in the absence of a subject. However, when calculating (including also interpolating) rates of change Rcs, the rates of change Rcs are acquired in the presence of the phantom Ph as shown in FIG. 13. Therefore, when the rates of change Rcs are obtained by actually moving the grid 6 as shown in FIG. 18 (c), it is preferable that that phantom Ph also is moved the same distance in the same direction as the direction of movement of the grid 6. In the case of the phantom Ph being an acrylic plate with a uniform thickness, it is not absolutely necessary to move the phantom Ph with movement of the grid 6, but the phantom Ph may be fixed.

Thus, instead of actually moving the X-ray tube 2 and obtaining parameters for each focal position Xf of the X-ray tube 2 relative to the FPD 3, correction is made using the parameters obtained after moving the grid 6, thereby obtaining the relationships between the parameters and the focal positions of the X-ray tube 2 relative to the FPD 3 matched therewith which are shown in FIG. 17.

The focal position Xf in the presence of the subject M calculated by the focal position calculating unit 43 in step S9 is matched with an applicable corresponding position in FIG. 17. The direct ray transmittances Cp and rates of change Rcs in that position are regarded as values obtained after the proofing, and these direct ray transmittances Cp and rates of change Rcs are acquired. When the focal position Xf calculated by the focal position calculating unit 43 is between discrete values in FIG. 17, the focal position Xf is determined by smoothing and interpolating calculation. The interpolating calculation is a two-dimensional interpolation which interpolates both SIDs and focal positions (in the direction of arrangement of the absorbing foil strips 6a). The simplest interpolating method is linear approximation interpolation. In this way, the parameters are obtained beforehand by actual measurement. An error of each parameter can be evaluated beforehand, and a required accuracy level can be secured by reducing the pitch (intervals) of the discrete positions.

(Step S11) Estimation and Interpolation of Intensities

As noted in step S4, the pixel values obtained in step S6 are equivalent to, the actual measurement intensities G after transmission through the grid 6 which are obtained by actual measurement in the presence of the subject M. Similarly, the pixel specifying unit 51 specifies the three adjoining pixels (n−1), n and (n+1) as a combination of three pixels. Based on the rates of change Rcs calculated by the rate of change calculating unit 56, the rates of change Rcs interpolated by the rate of change interpolating unit 57, or the rates of change Rcs proofed by the parameter proofing unit 45, the direct ray transmittances Cp calculated by the transmittance calculating unit 52, the direct ray transmittances Cp interpolated by the transmittance interpolating unit 43, or the direct ray transmittances Op proofed by the parameter proofing unit 45, the second intensity estimating unit 54 again estimates transmission scattered ray intensities Sc and estimated direct ray intensities P at the three adjoining pixels (n−1), n and (n+1) specified by the pixel specifying unit 51.

As in step S4, the transmission scattered ray intensities Sc and estimated direct ray intensities P are estimated by solving simultaneous equations. Differences to step S4 lie in that a parameter consisting of the rates of change Rcs is taken into consideration, and that the equations concerning the transmission scattered ray intensities Sc and estimated direct ray intensities P are different. The aspects common to step S4 will not be described.

In step S11, the transmission scattered ray intensities Sc are transmission scattered ray intensities where there is no foil nonuniformity such as deformation of the absorbing foil strips of the grid 6 and the installation condition is ideal. The transmission scattered ray intensities Sc vary smoothly where, apart from the rates of change due to nonuniformity of the grid 6, the subject is a water column (e.g. water cylinder) or a human body and the radiation is X-rays or gamma rays. Thus, the transmission scattered ray intensities Sc are considered equal among the three adjoining pixels, as expressed by the following equation (1)".

$$Sc_{n-1} = Sc_n = Sc_{n+1} \tag{1}$$

The actual measurement intensities G are expressed by the following simultaneous equations (2)"-(4)" for the three adjoining pixels (n−1), n and (n+1), showing that each actual measurement intensity G is equal to a sum of the product of estimated direct ray intensity P and direct ray transmittance Cp, and the product of transmission scattered ray intensity Sc and rate of change Rcs:

$$G_{n+1} = P_{n+1} \cdot Cp_{n+1} + Sc_{n+1} \cdot Rcs_{n+1} \tag{2}''$$

$$G_n = P_n \cdot Cp_n + Sc_n \cdot Rcs_n \tag{3}''$$

$$G_{n-1} = P_{n-1} \cdot Cp_{n-1} + Sc_{n-1} \cdot RcS_{n-1} \tag{4}''$$

As distinct from the case of the phantom Ph in the form of an acrylic plate in step S3, the estimated direct ray intensity P at each pixel is variable due to the shape and material of the subject M. The variations can be expressed by interpolating calculations of the estimated direct ray intensities P at adjoining pixels. In this embodiment, it is assumed that the variations in the estimated direct ray intensities P within the three adjoining pixels (n−1), n and (n+1) can be linearly approximated as in the following the equation (5)":

$$P_n = (P_{n+1} + P_{n-1})/2 \tag{5}''$$

As a method of interpolating the estimated direct ray intensities P, Lagrange interpolation, for example, may be used as noted in connection with the interpolation of the direct ray transmittances Cp and the interpolation of transmission scattered ray intensities Sc in step S4. The method is not limited to equation (5)" above, but any commonly used method of interpolation may be employed.

By solving simultaneous equations obtained from such equations (1)"-(5)" noted above, the estimated direct ray intensities $P_{n-1}$, $P_n$ and $P_{n-1}$, transmission scattered ray intensity $Sc_n$ ($=Sc_{n+1}=Sc_{n-1}$) are calculated as in the following equations (6)"-(9)":

$$Sc_n = G_{n+1}/Rcs_{n+1} - \{(Cp_n \cdot Rcs_{n-1} - 2Cp_{n-1} \cdot Rcs_n) \cdot G_{n+1} + 2Cp_{n-1} \cdot Rcs_{n+1} \cdot G_n - Cp_n \cdot Rcs_{n+1} \cdot G_{n-1}\}/\\ (CP_{n+1} \cdot Cp_n \cdot Rcs_{n+1} \cdot Rcs_{n-1} - 2Cp_{n+1} \cdot Cp_{n-1} \cdot\\ Rcs_{n+1} \cdot Rcs_n + Cp_n \cdot Cp_{n-1} \cdot Rcs_{n+1}^2) \quad (6)"$$

$$P_{n-1} \cdot Cp_n \cdot Rcs_{n-1} \cdot 2Cp_{n-1} \cdot Rcs_n) \cdot G_{n+1} + 2Cp_{n-1}\\ Rcs_{n+1} \cdot G_n - Cp_n \cdot Rcs_{n+1} \cdot G_{n-1}\}/(Cp_{n+1} \cdot Cp_n \cdot\\ Rcs_{n-1} - 2Cp_{n+1} \cdot Cp_{n-1} \cdot Rcs_n + Cp_n \cdot Cp_n \cdot Rcs_{n+1}) \quad (7)"$$

$$P \cdot G_n / Cp_n Rcs_n \cdot G_{n+1}/Rcs_{n+1} \cdot Cp_n \cdot Rcs_{n-1} - 2Cp_{n-1} \cdot Rcs_n) \cdot\\ G_{n+1} + 2Cp_{n-1} \cdot Rcs_{n+1} \cdot G_n - Cp_n \cdot Rcs_{n+1} \cdot G_{n-1}\}/\\ (Cp_{n+1} \cdot Cp_n \cdot Rcs_{n+1} \cdot Rcs_{n-1} \cdot 2Cp_{n+1} \cdot Cp_{n-1} \cdot\\ Rcs_{n+1} \cdot Rcs_n + Cp_n \cdot Cp_{n-1} \cdot Rcs_{n+1}^2)] \quad (8)"$$

$$P + G_{n+1}/Cp_{n+1} \cdot Rcs_{n-1} \cdot [\{Cp_n \cdot Rcs_{n-1} \cdot 2Cp_{n-1} \cdot Rcs_n \cdot\\ G_{n+1} \cdot 2Cp_{n-1} \cdot Rcs_{n+1} \cdot G_n \cdot Cp_n \cdot Rcs_{n+1} \cdot G_{n-1}\}/\\ (Cp_{n+1} \cdot Cp_n \cdot Rcs_{n+1} \cdot Rcs_{n-1} \cdot 2Cp_{n+1} \cdot Cp_{n-1} \cdot\\ Rcs_{n+1} \cdot Rcs_n \cdot Cp_n \cdot Cp_{n-1} \cdot Rcs_{n+1}^2)] \quad (9)"$$

The estimated direct ray intensities $P_{n-1}$, $P_n$ and $P_{n+1}$ and transmission scattered ray intensity $Sc_n$ ($=Sc_{n+1}=Sc_{n-1}$) derived from the above equations (6)"-(9)" are values calculated when the denominator included in the solution of the above simultaneous equations (1)"-(5)" is not "0".

When the denominator included in the solution of the above simultaneous equations (1)"-(5)" is "0", the above simultaneous equations (1)"-(5)" cannot be solved. Thus, with the three pixels (n−1), n and (n+1) forming the combination resulting in the denominator "0", the estimated direct ray intensities $P_{n-1}$, $P_n$ and $P_{n+1}$ or the transmission scattered ray intensities $Sc_{n-1}$, $Sc_n$ and $Sc_{n+1}$ cannot be calculated, and thus cannot be estimated. There are the following methods 1) and 2), for example, for estimating the estimated direct ray intensities $P_{n-1}$, $P_n$ and $P_{n+1}$ and the transmission scattered ray intensities $Sc_{n-1}$, $Sc_n$ and $Sc_{n+1}$ in the case of the three pixels (n−1), n and (n+1) forming the combination resulting in the denominator "0".

The method 1) determines the transmission scattered ray intensities Sc first. Since the transmission scattered ray intensities Sc assume that there is no deformation of the absorbing foil strips of the grid 6 and the installation condition is ideal, a plurality of transmission scattered ray intensities $Sc_n$ acquired when the denominator is not "0" are first used in appropriate smoothing and interpolating calculations to obtain transmission scattered ray intensities $Sc_n \sim$ for all the pixels, including those pixels for which the transmission scattered ray intensities Sc are not yet obtained because the denominator is "0". As noted in connection with the above equation (1)", variations are smooth where the subject is a water column (e.g. water cylinder) or a human body and the radiation is X-rays or gamma rays. And smoothing is effective in reducing variations due to statistical fluctuation errors. Thus, the values $Sc_n \sim$ obtained are close to the true values of transmission scattered ray intensities $Sc_n$. The transmission scattered ray intensities $Sc_n \sim$ obtained in this way are substituted into the above equation (3) for all the pixels, thereby obtaining the estimated direct ray intensities $P_n$ directly. As noted above, this method provides a great advantage of causing no deterioration in the resolution of images of the estimated direct ray intensities P since smoothing and interpolating calculations are not carried out from the values of the pixels for which the denominator is not "0".

The method 2) is a method of interpolating estimated direct ray intensities $P_{n-1}$, $P_n$ and $P_{n+1}$ not yet obtained, as in equation (5)" above, using the estimated direct ray intensities $P_{n-1}$, $P_n$ and $P_{n+1}$ already derived from equations (7) (9)" above. That is, the intensity interpolating unit 55 interpolates the estimated direct ray intensities $P_{n-1}$, $P_n$ and $P_{n+1}$ estimated by the second intensity estimating unit 54. This interpolation, as long as it is a usual interpolation, is not limited to the foregoing equation (5)". The estimated direct ray intensities $P_{n-1}$, $P_n$ and $P_{n+1}$ interpolated by the intensity interpolating unit 55 are fed to the display 5, for example.

Thus, as described above, and as in step S4, the transmission scattered ray intensities $Sc_n$ may be obtained first, or the estimated direct ray intensities $P_n$ may be obtained first.

Thus, through steps S1-S11, by using as pixel values the estimated direct ray intensities $P_n$ obtained in step S11, an X-ray image is appropriately obtained with reduced false images due to scattered rays and the grid 6. This X-ray image may be outputted to and displayed on the display 5 noted hereinbefore, may be written and stored in a storage medium represented by a RAM (Random-Access Memory) or the like to be read therefrom as necessary, or may be printed out by a printing device represented by a printer. When the transmission scattered ray intensities $Sc_n$ are obtained before the estimated direct ray intensities $P_n$ by the method 1) in step S11, the X-ray image may be outputted to the display 5, a storage medium and/or a printing device after the estimated direct ray intensities $P_n$, are obtained.

According to the X-ray imaging apparatus in this embodiment, the grid 6 is constructed to have the direction of arrangement (Y-direction) of the absorbing foil strips 6a, which absorb scattered rays (scattered X-rays), parallel to the direction of rows, of the direction of rows and the direction of columns, of the detecting elements d, and to have each absorbing foil strip 6a arranged parallel to the detecting plane of the FPD 3. The Y-direction adjust screws 60y of the moving mechanism 60 move the grid 6 parallel to the direction of arrangement (Y-direction) of the absorbing foil strips 6a. Therefore, when the Y-direction adjust screws 60y move the grid 6 a predetermined distance and X-rays are emitted from the X-ray tube 2, the physical quantities calculated by the physical quantity calculating device (transmittance calculating unit 52, transmittance interpolating unit 53, rate of change calculating unit 56 and rate of change interpolating unit 57 in this embodiment), i.e. the parameters (the direct ray transmittances Cp and rates of change Rcs in this embodiment), are obtained when X-rays are emitted from the X-ray tube 2 in the state of the grid 6 having been moved the above predetermined distance by the Y-direction adjust screws 60y. On the other hand, assuming that the X-ray tube 2 is moved the predetermined distance in the opposite direction (the opposite direction being $B^-$ direction when the direction of movement by the Y-direction adjust screws 60y is $B^+$ direction) to the direction of movement (e.g. $B^+$ direction) by the Y-direction adjust screws 60y, the parameters which should be obtained on this assumption can be considered the same as the parameters calculated by the physical quantity calculating device (the transmittance calculating unit 52, transmittance interpolating unit 53, rate of change calculating unit 56 and rate of change interpolating unit 57 in this embodiment) when X-rays are emitted from the X-ray tube 2 in the state of the grid 6 having been moved the above predetermined distance by the Y-direction adjust screws 60y. Therefore, the correcting unit 44 corrects the parameters which should be obtained on the assumption, as the parameters calculated by the physical quantity calculating device (the transmittance calculating unit 52, transmittance interpolating unit 53, rate of change calculating unit 56 and rate of change interpolating unit 57 in this embodiment) when X-rays are emitted from the X-ray tube 2 in the state of the grid 6 having been moved the above predetermined distance by the Y-direction adjust screws 60y, which allows only the grid 6 to be moved, instead of moving the X-ray tube 2. Therefore, parameters equivalent to the parameters which should be obtained when the X-ray tube 2 is moved are obtained by moving the grid 6, and position shifting can be reduced.

In this embodiment, the moving mechanism 60 is constructed capable of moving the grid 6 parallel to the direction of arrangement (Y-direction) of the absorbing foil strips 6a by an integral multiple (Wd×m when the integer is set to m) of the intervals between the pixels (i.e. pixel pitch Wd) forming an X-ray image. The correcting unit 44 corrects the parameters obtained on the assumption that the X-ray tube 2 is moved an amount corresponding to the above integral number of pixels (m pixels here) in the opposite direction (the opposite direction being B⁻ direction when the direction of movement by the Y-direction adjust screws 60y is B⁺ direction) to the direction of movement (e.g. B⁺ direction) by the Y-direction adjust screws 60y of the moving mechanism 60 (see FIG. 18 (b)), as the parameters obtained when X-rays are emitted from the X-ray tube 2 in the state of the grid 6 having been moved the amount corresponding to the integral number of pixels (m pixels) by the Y-direction adjust screws 60y. When the predetermined distance of movement by the Y-direction adjust screws 60y is set to the integral multiple (Wd×m) of the intervals between the pixels as described above, the interval between the position to which the X-ray tube 2 is virtually moved and the position to which the grid 6 is actually moved is related to the integral number of pixels. Thus, the parameters can be corrected accurately with no position shifting between the pixels.

In this embodiment, the physical quantities (parameters) are the direct ray transmittances Cp which are transmittances before transmission and after transmission of direct rays (direct X-rays) through the grid 6 obtained by actual measurement in the absence of a subject, and the rates of change Rcs relating to the transmission scattered ray intensities Sc which are scattered ray (scattered X-ray) intensities after transmission through the grid 6 obtained by actual measurement in the presence of a subject. When the parameters are the direct ray transmittances Cp and the rates of change Rcs (relating to the transmission scattered ray intensities Sc), the transmittance calculating unit 52 and transmittance interpolating unit 53 obtain the direct ray transmittances Cp, while the rate of change calculating unit 56 and rate of change interpolating unit 57 obtain the rates of change Rcs. The correcting unit 44 corrects the direct ray transmittances Cp and the rates of change Rcs obtained on the assumption that the X-ray tube 2 is moved the predetermined distance (Wd×m in this embodiment) in the opposite direction (the opposite direction being B⁻ direction when the direction of movement by the Y-direction adjust screws 60y is B⁺ direction) to the direction of movement (e.g. B⁺ direction) by the Y-direction adjust screws 60y, as the direct ray transmittances Cp and the rates of change Rcs obtained when X-rays are emitted from the X-ray tube 2 in the state of the grid 6 having been moved the predetermined distance (Wd×m) by the Y-direction adjust screws 60y. By using the direct ray transmittances Cp and the rates of change Rcs corrected as described above in the X-ray imaging (in this embodiment, the positional relationships in FIG. 17), false image processing is carried out with the direct ray transmittances Cp and rates of change Rcs having no position shifting, thereby to remove false images due to position shifting.

This invention is not limited to the foregoing embodiwent, but may be modified as follows:

(1) The foregoing embodiment has been described taking X-rays as an example of radiation. However, the invention is applicable to radiation other than X-rays (such as gamma rays).

(2) In the foregoing embodiment, the radiographic apparatus is constructed for medical use to conduct radiography of a patient placed on the top board 1 as shown in FIG. 1. This is not limitative. For example, the apparatus may be constructed like a nondestructive testing apparatus for industrial use which conducts radiography of an object (in this case, a subject tested) conveyed on a belt, or may be constructed like an X-ray CT apparatus for medical use.

Figure 19:
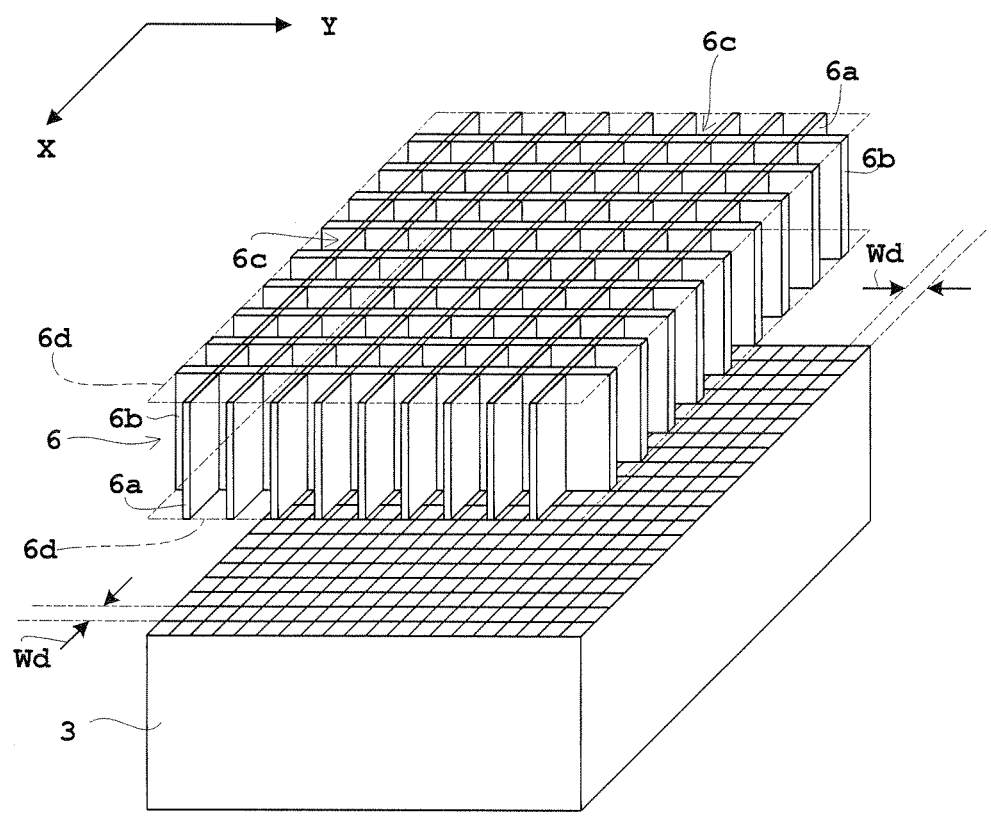
FIG. 19 is a schematic view of a cross grid in a modified embodiment.

(3) The foregoing embodiment employs an air grid as the scattered radiation removing device represented by a grid, but the grid is not limited to the air grid. The grid may have, in place of the voids, an intermediate material such as aluminum or organic substance which transmits radiation represented by X-rays. Further, a cross grid may be employed as shown in FIG. 19. Specifically, while the absorbing foil strips 6a and intermediate layers 6c extending in the X-direction in FIG. 3 are arranged alternately in order in the Y-direction in FIG. 3, absorbing foil strips 6b and intermediate layers 6c extending in the Y-direction in FIG. 3 are arranged alternately in order in the X-direction in FIG. 3, such that the absorbing foil strips 6a and absorbing foil strips 6b cross one another. The X-direction in FIG. 3 is parallel to the rows of detecting elements d of FPD 3 (see FIG. 2), while the Y-direction in FIG. 3 is parallel to the columns of detecting elements d of FPD 3 (see FIG. 2). Therefore, the directions of arrangement of the absorbing foil strips 6a and 6b are parallel to both the rows and columns of detecting elements d of FPD 3.

(4) The foregoing embodiment provides the marking absorbers 7, but these are not absolutely necessary.

(5) In the foregoing embodiment, the physical quantities (parameters) processed by the correcting unit 44 are the direct ray transmittances and the rates of change of the transmission scattered ray intensities. They may be only the direct ray transmittances or only the rates of change of the transmission scattered ray intensities.

(6) In the foregoing embodiment, the physical quantities (parameters) processed by the correcting unit 44 are the direct ray transmittances and the rates of change of the transmission scattered ray intensities, but these are not limitative. Any physical quantities relating to radiation intensity are acceptable, which may, for example, be pixel values (intensities) allotted to the respective pixels forming a radiological image (X-ray image in the embodiment) and corresponding to radiation intensities (X-ray image in the embodiment) detected by the radiation detecting device (FPD in the embodiment). When the parameters are pixel values, the physical quantity calculating device calculates the pixel values. The correcting device (correcting unit 44 in the embodiment) corrects the pixel values obtained on the assumption that the radiation emitting device (X-ray tube 2 in the embodiment) is moved over the number of pixels corresponding to the predetermined distance in the opposite direction to the direction of movement by the moving device (Y-direction adjust screws 60y of the moving mechanism 60 in the embodiment), as the pixel values calculated by the physical quantity calculating device when radiation (X-rays in the embodiment) is emitted from the radiation emitting device (X-ray tube 2 in the embodiment) in the state of the scattered radiation removing device (grid 6 in the embodiment) having been moved the number of pixels corresponding the predetermined distance by the moving device (Y-direction adjust screws 60y). When calculating the pixel values in the presence of the subject M, it is preferred that the subject M is moved as interlocked to the movement of the grid 6.

The invention claimed is:

1. A radiographic apparatus for obtaining a radiological image, comprising:
   a radiation emitting device for emitting radiation;
   a scattered radiation removing device for removing scattered radiation; and
   a radiation detecting device having a plurality of detecting elements arranged in rows and columns for detecting the radiation;
   wherein the scattered radiation removing device is constructed to have a direction of arrangement of absorbing layers, which absorb the scattered radiation, parallel to at least one of a direction of the rows and a direction of the columns of the detecting elements, and to have each of the absorbing layers arranged parallel to a detecting plane of the radiation detecting device; and
   wherein the radiographic apparatus further comprises:
   a moving device for moving only the scattered radiation removing device parallel to the direction of arrangement of the absorbing layers such that the positional relationship of the scattered radiation removing device with respect to each of the radiation emitting device and the radiation detecting device is altered;
   a physical quantity calculating device for calculating physical quantities relating to radiation intensity based on detection by the radiation detecting device of the radiation after transmission through the scattered radiation removing device; and
   a correcting device for calculating physical quantities obtained on an assumption that the radiation emitting device is moved a predetermined distance in a direction opposite to a direction of movement by the moving device, from the physical quantities calculated by the physical quantity calculating device when radiation is emitted from the radiation emitting device in a state of the scattered radiation removing device having been moved the predetermined distance by the moving device.

2. The radiographic apparatus according to claim 1, wherein the moving device is constructed capable of moving the scattered radiation removing device parallel to the direction of arrangement of the absorbing layers by an integral multiple of intervals between pixels forming the radiological image, and the correcting device is arranged to correct physical quantities obtained on an assumption that the radiation emitting device is moved an amount corresponding to the integral number of pixels in the direction opposite to the direction of movement by the moving device, as the physical quantities calculated by the physical quantity calculating device when radiation is emitted from the radiation emitting device in a state of the scattered radiation removing device having been moved the amount corresponding to the integral number of pixels by the moving device.

3. The radiographic apparatus according to claim 1, wherein the physical quantities are direct ray transmittances which are transmittances before transmission and after transmission of direct radiation through the scattered radiation removing device obtained by actual measurement in the absence of a subject, the physical quantity calculating device is arranged to calculate the direct ray transmittances, and the correcting device is arranged to correct direct ray transmittances obtained on an assumption that the radiation emitting device is moved the predetermined distance in the direction opposite to the direction of movement by the moving device, as the direct ray transmittances calculated by the physical quantity calculating device when radiation is emitted from the radiation emitting device in a state of the scattered radiation removing device having been moved the predetermined distance by the moving device.

4. The radiographic apparatus according to claim 1, wherein the physical quantities are rates of change relating to transmission scattered ray intensity which is scattered radiation intensity after transmission through the scattered radiation removing device, the physical quantity calculating device is arranged to calculate the rates of change, and the correcting device is arranged to correct rates of change obtained on an assumption that the radiation emitting device is moved the predetermined distance in the direction opposite to the direction of movement by the moving device, as the rates of change calculated by the physical quantity calculating device when radiation is emitted from the radiation emitting device in a state of the scattered radiation removing device having been moved the predetermined distance by the moving device.

5. The radiographic apparatus according to claim 1, wherein the physical quantities are direct ray transmittances which are transmittances before transmission and after transmission of direct radiation through the scattered radiation removing device obtained by actual measurement in the absence of a subject, and rates of change relating to transmission scattered ray intensity which is scattered radiation intensity after transmission through the scattered radiation removing device obtained by actual measurement in the presence of the subject, the physical quantity calculating device is arranged to calculate the direct ray transmittances and the rates of change, and the correcting device is arranged to correct direct ray transmittances and rates of change obtained on an assumption that the radiation emitting device is moved the predetermined distance in the direction opposite to the direction of movement by the moving device, as the direct ray transmittances and the rates of change calculated by the physical quantity calculating device when radiation is emitted from the radiation emitting device in a state of the scattered radiation removing device having been moved the predetermined distance by the moving device.

6. The radiographic apparatus according to claim 1, wherein the physical quantities are pixel values allotted to respective pixels forming the radiological image and corresponding to radiation intensities detected by the radiation detecting device, the physical quantity calculating device is arranged to calculate the pixel values, and the correcting device is arranged to correct pixel values obtained on an assumption that the radiation emitting device is moved over the number of pixels corresponding to the predetermined distance in the direction opposite to the direction of movement by the moving device, as the pixel values calculated by the physical quantity calculating device when radiation is emitted from the radiation emitting device in a state of the scattered radiation removing device having been moved the number of pixels corresponding to the predetermined distance by the moving device.

* * * * *